United States Patent
Lin et al.

(10) Patent No.: US 9,474,792 B2
(45) Date of Patent: Oct. 25, 2016

(54) METHOD OF TREATING METABOLIC DISORDERS USING PLA2G12A POLYPEPTIDES AND PLA2G12A MUTANT POLYPEPTIDES

(71) Applicant: AMGEN INC., Thousand Oaks, CA (US)

(72) Inventors: Daniel C. H. Lin, Redwood City, CA (US); Jinghong Wang, Palo Alto, CA (US); Yang Li, Mountain View, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 14/772,910

(22) PCT Filed: Mar. 13, 2014

(86) PCT No.: PCT/US2014/026736
§ 371 (c)(1),
(2) Date: Sep. 4, 2015

(87) PCT Pub. No.: WO2014/151962
PCT Pub. Date: Sep. 25, 2014

(65) Prior Publication Data
US 2016/0008439 A1    Jan. 14, 2016

Related U.S. Application Data

(60) Provisional application No. 61/793,503, filed on Mar. 15, 2013.

(51) Int. Cl.
*A61K 38/46*     (2006.01)
*A61B 5/145*     (2006.01)
*C12N 9/20*     (2006.01)

(52) U.S. Cl.
CPC ......... *A61K 38/465* (2013.01); *A61B 5/14532* (2013.01); *C12N 9/20* (2013.01); *C12Y 301/01004* (2013.01)

(58) Field of Classification Search
None
See application file for complete search history.

(56) References Cited

U.S. PATENT DOCUMENTS 3,773,919 A     11/1973  Boswell et al.
2014/0099295 A1*  4/2014  Tian ................. C12Y 301/0100
                                              424/94.6

FOREIGN PATENT DOCUMENTS

| EP | 00/58481 A1 | 8/1982 | |
| EP | 00/88046 A2 | 9/1983 | |
| EP | 00/36676 B2 | 7/1984 | |
| EP | 01/43949 A1 | 6/1985 | |
| WO | 93/15722 A1 | 8/1993 | |
| WO | 2012/151159 A1 | 11/2012 | |
| WO | WO2012151159 A1 * | 11/2012 | ............. A61K 38/46 |
| WO | 2014/151962 A1 | 9/2014 | |

OTHER PUBLICATIONS

NCBI PLA2G12A Alignment.*
Berge et al., J. Pharm. Sci., 1977, 66:1,1-19.
Bootcov MR, Proc. Natl. Acad. Sci. U.S., 1997, 94:11514-11519.
Carrillo et al., SIAM J. Applied Math. 1988, 48:1073.
Dayhoff et al., Atlas of Protein Sequence and Structure, 1978, 5:345-352.
Devereux et al., Nucl. Acid Res., 1984, 12:387.
Eppstein et al., Proc. Natl. Acad. Sci. U.S., 1985, 82: 3688-92.
Gribskov et al., Sequence Analysis Primer, 1991.
Fairlie WD, Gene, 2000, 254: 67-76.
Freiberg et al., Int. J. Pharm. 2004, 282: 1-18.
Henikoff et al., Proc. Natl. Acad. Sci. U.S., 1992, 89:10915-10919.
International Search Report: PCT/US2014/026736 dated Jul. 4, 2014.
Langer, Chem. Tech., 1982, 12: 98-105.
Langer et al., J. Biomed. Mater. Res. 1981, 15: 167-277.
Lesk, A. M., ed., Computational Molecular Biology, New York: Oxford University Press, 1988.
Murakami et al., J. Biol Chem, 2003, 278:10657-67.
Needleman et al., J. Mol. Biol., 1970, 48:443-453.
Rouault et al., Biochemistry 2003, 42:11494-11503.
Sambrook, et al., Molecular Cloning: A Laboratory Manual 2nd, ed., Cold Spring Harbor Laboratory, Cold Spring Harbor Laboratory Press, Cold Spring Harbor, N.Y., 1989.
Valentin et al., J. Biol Chem. 2000, 275:7492-7496.
Wischke & Schwendeman, Int. J. Pharm. 2008, 364: 298-327.

* cited by examiner

*Primary Examiner* — Satyanarayana R Gudibande
*Assistant Examiner* — Jia-Hai Lee

(57) ABSTRACT

Methods of treating or ameliorating metabolic diseases using a PLA2G12A polypeptide or PLA2G12A mutant polypeptide are provided. In various embodiments the metabolic disease or disorder is type 2 diabetes mellitus, obesity, dyslipidemia elevated glucose levels, elevated insulin levels and diabetic nephropathy.

24 Claims, 12 Drawing Sheets

A

Two-way ANOVA comparing to vector control

* p < 0.05
** p < 0.01
*** p < 0.001
**** p < 0.0001

B

US 9,474,792 B2

METHOD OF TREATING METABOLIC DISORDERS USING PLA2G12A POLYPEPTIDES AND PLA2G12A MUTANT POLYPEPTIDES

This application is a national stage application under 35 U.S.C. §371 of International Application No. PCT/US2014/026736, having an international filing date of Mar. 13, 2014, which claims the benefit of U.S. Provisional Patent Application No. 61/793,503, filed on Mar. 15, 2013 which are hereby incorporated by reference.

The present application is being filed along with a Sequence Listing in electronic format. The Sequence Listing is provided as a file entitled A-1824-US-PCT_SeqList.txt, created Jun. 5, 2015 which is 33 KB size. The information in the electronic format of the Sequence Listing is incorporated herein by reference in its entirety.

FIELD OF THE INVENTION

The disclosed invention relates to the treatment or amelioration of a metabolic disorder, such as Type 2 diabetes, elevated glucose levels, elevated insulin levels, dyslipidemia, obesity or diabetic nephropathy, by administering a therapeutically effective amount of a PLA2G12A polypeptide or PLA2G12A mutant polypeptide to a subject in need thereof.

BACKGROUND OF THE INVENTION

Phospholipase A2, group XIIA (PLA2G12A) is a secreted polypeptide that belongs to the superfamily of phospholipase $A_2$ (PLA2) enzymes. It is also called phospholipase A2, group XIIA, Group XIIA secretory phospholipase A2, ROSSY, FKSG38, and UNQ2519/PRO6012.

Phospholipase A2 enzymes, including PLA2G12A, catalyze the calcium-dependent hydrolysis of phospholipids at the sn-2 position to yield fatty acids and lysophospholipids. The active site of PLA2G12A comprises a His-Asp dyad. However, PLA2G12A has relatively low phospholipase activity in a standard Phospholipase A2 assay and is structurally and functionally distinct from other secreted phospholipase A2s. Gelb et al., 2000, *J. Biol Chem.*, 275:7492-7496. Rouault et al., 2003, *Biochemistry* 42:11494-11503; Murakami et al., 2003, *J. Biol Chem*, 218:10657-67.

Human PLA2G12A gene is located on chromosome 4q25. The mature, secreted, PLA2G12A polypeptide shares low homology with other family members except for the conserved $Ca^{2+}$-binding loop and catalytic site. Murakami et al., 2003.

Full length PLA2G12A contains a predicted signal sequence which is cleaved to release the mature peptide. Human full-length precursor contains 189 amino acids, including a predicted 22 amino acid signal sequence. The human mature polypeptide contains 167 amino acids. PLA2G12A is abundantly expressed in heart, skeletal muscle, kidney, liver and pancreas. PLA2G12A is also present in brain, liver, small intestine, lung and placenta. Gelb et al.

The present disclosure provides nucleic acid molecules encoding PLA2G12A mutant peptides, PLA2G12A mutant polypeptides, pharmaceutical compositions comprising PLA2G12A mutant polypeptides, and methods for treating metabolic disorders using such nucleic acids, polypeptides, or pharmaceutical compositions.

SUMMARY OF THE INVENTION

A method of treating a metabolic disorder is provided. In one embodiment, the method comprises administering to a subject in need thereof a therapeutically effective amount of an isolated PLA2G12A polypeptide (e.g., a human PLA2G12A polypeptide). In various embodiments, the metabolic disorder is type 2 diabetes, dyslipidemia, insulin resistance, metabolic syndrome, obesity or diabetic nephropathy. In other embodiments, the metabolic disorder comprises a condition in which the subject has a fasting blood glucose level of greater than or equal to 100 mg/dL. The subject with respect to which the method is performed can be a mammal, for example a human. In specific embodiments, the PLA2G12A polypeptide comprises an amino acid sequence selected from the group consisting of SEQ ID NOs: 1 and 3 and/or is encoded by the nucleic acid sequence comprising a sequence selected from SEQ ID NOs: 2 and 4. In some embodiments, the PLA2G12A polypeptide is administered in the form of a pharmaceutical composition comprising the PLA2G12A polypeptide in admixture with a pharmaceutically-acceptable carrier. In yet other embodiments the provided method further comprises the step of determining the subject's blood glucose level at a timepoint subsequent to the administration. In still other embodiments the method further comprises the step of determining the subject's serum insulin level at a timepoint subsequent to the administration.

Also provided is a method of treating a metabolic disorder comprising administering to a subject in need thereof a therapeutically effective amount of an isolated PLA2G12A polypeptide comprising an amino acid sequence that has at least 90% sequence identity with a sequence selected from the group consisting of SEQ ID NOs:1 and 3. In various embodiments, the metabolic disorder is type 2 diabetes, dyslipidemia, insulin resistance, metabolic syndrome, obesity or diabetic nephropathy. In other embodiments, the metabolic disorder comprises a condition in which the subject has a fasting blood glucose level of greater than or equal to 100 mg/dL. The subject with respect to which the method is performed can be a mammal, for example a human. In some embodiments the PLA2G12A polypeptide is administered in the form of a pharmaceutical composition comprising the PLA2G12A polypeptide in admixture with a pharmaceutically-acceptable carrier. In yet other embodiments the provided method further comprises the step of determining the subject's blood glucose level at a timepoint subsequent to the administration. In still other embodiments the method further comprises the step of determining the subject's serum insulin level at a timepoint subsequent to the administration.

In another embodiment, the method comprises administering to a subject in need thereof a therapeutically effective amount of an isolated PLA2G12A mutant polypeptide comprising an amino acid sequence that has at least 90% sequence identity with a sequence selected from the group consisting of SEQ ID NOs:9, 11, 13, 15, 17, 19, 21, 23, 25 and 27. In various embodiments, the metabolic disorder is type 2 diabetes, dyslipidemia, insulin resistance, metabolic syndrome, obesity or diabetic nephropathy. In other embodiments, the metabolic disorder comprises a condition in which the subject has a fasting blood glucose level of greater than or equal to 100 mg/dL. The subject with respect to which the method is performed can be a mammal, for example a human. In specific embodiments, the PLA2G12A mutant protein comprises a sequence selected from SEQ ID NOs:9, 11, 13, 15, 17, 19, 21, 23, 25 and 27 and/or is encoded by the nucleic acid sequence comprising a sequence selected from SEQ ID NOs:10, 12, 14, 16, 18, 20, 22, 24, 26 and 28. In some embodiments, the PLA2G12A mutant polypeptide is administered in the form of a pharmaceutical composition comprising the PLA2G12A mutant polypeptide in admixture with a pharmaceutically-acceptable carrier. In yet other embodiments the provided method further comprises the step of determining the subject's blood glucose level at a timepoint subsequent to the administration. In still other embodiments the method further comprises the step of determining the subject's serum insulin level at a timepoint subsequent to the administration.

Also provided are isolated PLA2G12A polypeptides (e.g., a human PLA2G12A polypeptide) and nucleic acid molecules encoding PLA2G12A polypeptides. In various embodiments, the isolated PLA2G12A polypeptide is selected from SEQ ID NOs: 1 and 3 and/or is encoded by the nucleic acid sequence comprising a sequence selected from SEQ ID NOs: 2 and 4. In other embodiments, the PLA2G12A polypeptide comprises a sequence that has at least 90% sequence identity with a sequence selected from SEQ ID NOs:1 and 3.

Also provided are PLA2G12A mutant polypeptides and nucleic acid molecules encoding PLA2G12A mutant polypeptides. In various embodiments, the PLA2G12A mutant polypeptide comprises a sequence selected from SEQ ID NOs:9, 11, 13, 15, 17, 19, 21, 23, 25 and 27 and/or is encoded by the nucleic acid sequence comprising a sequence selected from SEQ ID NOs:10, 12, 14, 16, 18, 20, 22, 24, 26 and 28. In other embodiments, the PLA2G12A mutant polypeptide comprises a sequence that has at least 90% sequence identity with a sequence selected from SEQ ID NOs:9, 11, 13, 15, 17, 19, 21, 23, 25 and 27.

Also provided are pharmaceutical compositions comprising a PLA2G12A polypeptide and/or a PLA2G12A mutant protein, as provided herein, and a pharmaceutically acceptable carrier.

DETAILED DESCRIPTION OF THE INVENTION

Figure 1:
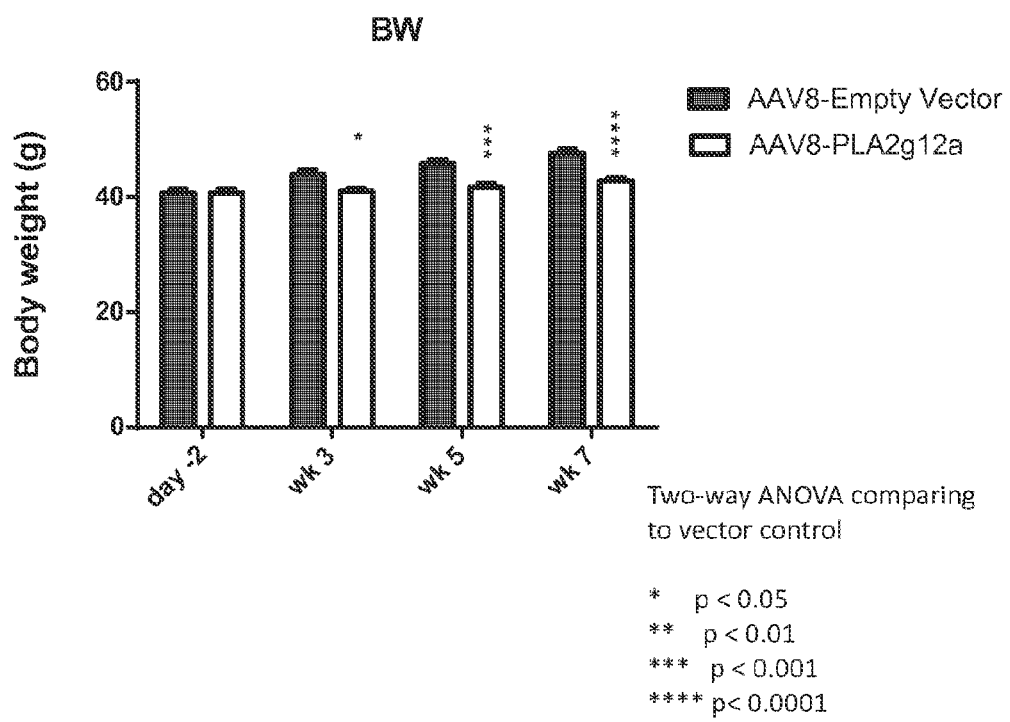
FIG. 1 is a bar graph showing body weight (g) of AAV8-PLA2G12A mice and AAV8-empty vector (control) mice. The body weight was measured two days before injection, and at week 3, week 5 and week 7 after injection.

The present disclosure provides a method of treating a metabolic disorder, such as Type 2 diabetes mellitus (referred to interchangeably herein as "type 2 diabetes"), elevated glucose levels, elevated insulin levels, dyslipidemia, insulin resistance, metabolic syndrome, diabetic nephropathy or obesity, by administering to a subject in need thereof a therapeutically effective amount of an isolated PLA2G12A polypeptide, e.g., human PLA2G12A polypeptide, and/or a PLA2G12A mutant polypeptide. Methods of administration and delivery are also provided.

The present disclosure also provides isolated PLA2G12A polypeptides, e.g., human PLA2G12A polypeptide, nucleic acid molecules encoding PLA2G12A polypeptides and pharmaceutical compositions comprising a PLA2G12A polypeptide.

The present disclosure also provides PLA2G12A mutant polypeptides, nucleic acid molecules encoding PLA2G12A mutant polypeptides and pharmaceutical compositions comprising a PLA2G12A mutant polypeptide.

Recombinant polypeptide and nucleic acid methods used herein, are generally those, set forth in Sambrook et al., *Molecular Cloning: A Laboratory Manual* (Cold Spring Harbor Laboratory Press, 1989) and subsequent editions or *Current Protocols in Molecular Biology* (Ausubel et al., eds., Green Publishers Inc. and Wiley and Sons 1994) and subsequent editions, both of which are incorporated herein by reference for any purpose.

I. GENERAL DEFINITIONS

Following convention, as used herein "a" and "an" mean "one or more" unless specifically indicated otherwise.

As used herein, the terms "amino acid" and "residue" are interchangeable and, when used in the context of a peptide or polypeptide, refer to both naturally occurring and synthetic amino acids, as well as amino acid analogs, amino acid mimetics and non-naturally occurring amino acids that are chemically similar to the naturally occurring amino acids.

The terms "naturally occurring amino acid" and "naturally encoded amino acid" are used interchangeably and refer to an amino acid that is encoded by the genetic code, as well as those amino acids that are encoded by the genetic code that are modified after synthesis, e.g., hydroxyproline. γ-carboxyglutamate, and O-phosphoserine.

An "amino acid analog" is a compound that has the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs can have modified R groups (e.g., norleucine) or modified peptide backbones, but will retain the same basic chemical structure as a naturally occurring amino acid.

An "amino acid mimetic" is a chemical compound that has a structure that is different from the general chemical structure of an amino acid, but that functions in a manner similar to a naturally occurring amino acid. Examples include a methacryloyl or acryloyl derivative of an amide, β-, γ-, δ-imino acids (such as piperidine-4-carboxylic acid) and the like.

The terms "non-naturally occurring amino acid" and "non-naturally encoded amino acid" are used interchangeably and refer to a compound that has the same basic chemical structure as a naturally occurring amino acid, but is not incorporated into a growing polypeptide chain by the translation complex. "Non-naturally occurring amino acid" also includes, but is not limited to, amino acids that occur by modification (e.g., posttranslational modifications) of a naturally encoded amino acid (including but not limited to, the 20 common amino acids) but are not themselves naturally incorporated into a growing polypeptide chain by the translation complex. A non-limiting lists of examples of non-naturally occurring amino acids that can be inserted into a polypeptide sequence or substituted for a wild-type residue in polypeptide sequence include β-amino acids, homoamino acids, cyclic amino acids and amino acids with derivatized side chains. Examples include (in the L-form or D-form; abbreviated as in parentheses): citrulline (Cit), homocitrulline (hCit), Nα-methylcitrulline (NMcCit), Nα-methylhomocitrulline (Nα-MeHoCit), ornithine (Orn), Nα-Methylornithine (Nα-MeOrn or NMeOrn), sarcosine (Sar), homolysine (hLys or hK), homoarginine (hArg or hR), homoglutamine (hQ), Nα-methylarginine (NMeR), Nα-methylleucine (Nα-MeL or NMeL), N-methylhomolysine (NMeHoK). Nα-methylglutamine (NMeQ), norleucine (Nle), norvaline (Nva), 1,2,3,4-tetrahydroisoquinoline (Tic), Octahydroindole-2-carboxylic acid (Oic), 3-(1-naphthyl) alanine (1-Nal), 3-(2-naphthyl)alanine (2-Nal), 1,2,3,4-tetrahydroisoquinoline (Tic), 2-indanylglycine (IgI), para-iodophenylalanine (pI-Phe), para-aminophenylalanine (4AmP or 4-Amino-Phe), 4-guanidino phenylalanine (Guf), glycyllysine (abbreviated "K(Nε-glycyl)" or "K(glycyl)" or "K(gly)"), nitrophenylalanine (nitrophe), aminophenylalanine (aminophe or Amino-Phe), benzylphenylalanine (benzylphe), γ-carboxyglutamic acid (γ-carboxyglu), hydroxyproline (hydroxypro), p-carboxyl-phenylalanine (Cpa), α-aminoadipic acid (Aad), Nα-methyl valine (NMeVal), N-α-methyl leucine (NMeLeu), Nα-methylnorleucine (NMeNle), cyclopentylglycine (Cpg), cyclohexylglycine (Chg), acetylarginine (acetylarg), α,β-diaminopropionoic acid (Dpr), α,γ-diaminobutyric acid (Dab), diaminopropionic acid (Dap), cyclohexylalanine (Cha), 4-methyl-phenyl-alanine (MePhe), β,β-diphenyl-alanine (BiPhA), aminobutyric acid (Abu), 4-phenyl-phenylalanine (or biphenylalanine; 4Bip), α-amino-isobutyric acid (Aib), beta-alanine, beta-aminopropionic acid, piperidinic acid, aminocaprioic acid, aminoheptanoic acid, aminopimelic acid, desmosine, diaminopimelic acid, N-ethylglycine, N-ethylaspargine, hydroxylysine, allo-hydroxylysine, isodesmosine, allo-isoleucine, N-methylglycine, N-methylisoleucine, N-methylvaline, 4-hydroxyproline (Hyp). γ-carboxyglutamate, ε-N,N,N-trimethyllysine, ε-N-acetyllysine, O-phosphoserine, N-acetylserine, N-formylmethionine, 3-methylhistidine, 5-hydroxylysine, ω-methylarginine, 4-Amino-O-Phthalic Acid (4APA), N-acetylglucosaminyl-L-serine, N-acetylglucosylaminyl-L-threonine, O-phosphotyrosine and other similar amino acids, and derivatized forms of any of those specifically listed.

The term "isolated nucleic acid molecule" refers to a single or double-stranded polymer of deoxyribonucleotide or ribonucleotide bases read from the 5' to the 3' end (e.g., a PLA2G12A nucleic acid sequence provided herein), or an analog thereof, that has been separated from at least about 50 percent of polypeptides, peptides, lipids, carbohydrates, polynucleotides or other materials with which the nucleic acid is naturally found when total nucleic acid is isolated from the source cells. Preferably, an isolated nucleic acid molecule is substantially free from any other contaminating nucleic acid molecules or other molecules that are found in the natural environment of the nucleic acid that would interfere with its use in polypeptide production or its therapeutic, diagnostic, prophylactic or research use.

The term "isolated polypeptide" refers to a polypeptide (e.g., a PLA2G12A polypeptide sequence provided herein) that has been separated from at least about 50 percent of polypeptides, peptides, lipids, carbohydrates, polynucleotides, or other materials with which the polypeptide is naturally found when isolated from a source cell. Preferably, the isolated polypeptide is substantially free from any other contaminating polypeptides or other contaminants that are found in its natural environment that would interfere with its therapeutic, diagnostic, prophylactic or research use.

The term "encoding" refers to a polynucleotide sequence encoding one or more amino acids. The term does not require a start or stop codon. An amino acid sequence can be encoded in any one of the different reading frames provided by a polynucleotide sequence.

The terms "identical" and percent "identity," in the context of two or more nucleic acids or polypeptide sequences, refer to two or more sequences or subsequences that are the same. "Percent identity" means the percent of identical residues between the amino acids or nucleotides in the compared molecules and is calculated based on the size of the smallest of the molecules being compared. For these calculations, gaps in alignments (if any) can be addressed by a particular mathematical model or computer program (i.e., an "algorithm"). Methods that can be used to calculate the identity of the aligned nucleic acids or polypeptides include those described in *Computational Molecular Biology*, (Lesk, A. M., ed.), (1988) New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., (1987) Sequence Analysis in Molecular Biology, New York: Academic Press; Sequence Analysis Primer, (Gribskov, M. and Devereux, J., eds.), 1991, New York: M. Stockton Press; and Carillo et al., (1988) *SIAM J. Applied Math.* 48:1073.

In calculating percent identity, the sequences being compared are aligned in a way that gives the largest match between the sequences. The computer program used to determine percent identity is the GCG program package, which includes GAP (Devereux et al., (1984) *Nucl. Acid Res.* 12:387; Genetics Computer Group, University of Wisconsin, Madison, Wis.). The computer algorithm GAP is used to align the two polypeptides or polynucleotides for which the percent sequence identity is to be determined. The sequences are aligned for optimal matching of their respective amino acid or nucleotide (the "matched span", as determined by the algorithm). A gap opening penalty (which is calculated as 3× the average diagonal, wherein the "average diagonal" is the average of the diagonal of the comparison matrix being used; the "diagonal" is the score or number assigned to each perfect amino acid match by the particular comparison matrix) and a gap extension penalty (which is usually ¹⁄₁₀ times the gap opening penalty), as well as a comparison matrix such as PAM 250 or BLOSUM 62 are used in conjunction with the algorithm. In certain embodiments, a standard comparison matrix (see, Dayhoff et al., (1978) *Atlas of Protein Sequence and Structure* 5:345-352 for the PAM 250 comparison matrix; Henikoff et al., (1992) *Proc. Natl. Acad. Sci. U.S.A.* 9:10915-10919 for the BLOSUM 62 comparison matrix) is also used by the algorithm.

Recommended parameters for determining percent identity for polypeptides or nucleotide sequences using the GAP program are the following:

Algorithm: Needleman et al., 1970, *J. Mol. Biol.* 48:443-453;

Comparison matrix: BLOSUM 62 from Henikoff et al., 1992, supra;

Gap Penalty: 12 (but with no penalty for end gaps)

Gap Length Penalty: 4

Threshold of Similarity: 0

Certain alignment schemes for aligning two amino acid sequences can result in matching of only a short region of the two sequences, and this small aligned region can have very high sequence identity even though there is no significant relationship between the two full-length sequences. Accordingly, the selected alignment method (e.g., the GAP program) can be adjusted if so desired to result in an alignment that spans at least 50 contiguous amino acids of the target polypeptide.

As used herein, the term "PLA2G12A polypeptide" (or "PLA2G12A") refers to a naturally-occurring (or "wild-type") polypeptide expressed in an animal (e.g., a mammal, such as a human, monkey, rabbit, mouse or rat. For purposes of this disclosure, the term "PLA2G12A polypeptide" can be used to refer to any full-length PLA2G12A polypeptide (e.g., SEQ ID NO: 1, which consist of 189 amino acid residues and which is encoded by the nucleotide sequence SEQ ID NO:2), the mature PLA2G12A polypeptide from which a signal sequence has been removed (e.g., SEQ ID NO:3, which consists of 167 amino acid residues and which is encoded by nucleotide sequence SEQ ID NO:4). The term PLA2G12A as used herein also includes naturally occurring alleles (e.g., naturally occurring allelic forms of human PLA2G12A polypeptide). PLA2G12A polypeptides may be isolated from a variety of sources, such as from human or non-human (e.g., mouse) tissues, or prepared by recombinant or synthetic methods. PLA2G12A polypeptides can but need not comprise an amino-terminal methionine, which may be introduced by engineering or as a result of an expression process (e.g., bacterial expression).

In various embodiments, a PLA2G12A polypeptide comprises an amino acid sequence that is at least about 85 percent identical to a naturally-occurring PLA2G12A polypeptide (e.g., SEQ ID NOs:1 or 3). In other embodiments, a PLA2G12A polypeptide comprises an amino acid sequence that is at least about 90 percent, or about 95, 96, 97, 98, or 99 percent identical to a naturally-occurring PLA2G12A polypeptide amino acid sequence (e.g., SEQ ID NOs:1 or 3). Such PLA2G12A polypeptides preferably, but need not, possess at least one activity of a wild-type PLA2G12A polypeptide, such as the ability to lower blood glucose, insulin or triglyceride levels; the ability to reduce body weight; or the ability to improve glucose tolerance or insulin sensitivity. The present invention also encompasses nucleic acid molecules encoding such PLA2G12A polypeptide sequences.

As used herein, the term "PLA2G12A mutant polypeptide" (or "mutant PLA2G12A") refers to a PLA2G12A polypeptide in which a naturally occurring PLA2G12A polypeptide sequence has been modified. Such modifications include, but are not limited to, one or more amino acid substitutions, including substitutions with non-naturally occurring amino acids non-naturally-occurring amino acid analogs and amino acid mimetics. For purposes of this disclosure, the term "PLA2G12A mutant polypeptide" can be used to refer to a so modified PLA2G12A polypeptide that includes a signal sequence, or predicted signal sequence (e.g., SEQ ID NO:9, which has the amino acid sequence of SEQ ID NO:1 with an H110L mutation, and which is encoded by the nucleotide sequence SEQ ID NO:10) or to a so modified PLA2G12A polypeptide from which a signal sequence, or predicted signal sequence, has been removed (e.g., SEQ ID NO: 11, which has the amino acid sequence of SEQ ID NO:3 with an H110L mutation, and which is encoded by nucleotide sequence SEQ ID NO:12). PLA2G12A mutant polypeptides may be prepared by recombinant or synthetic methods. PLA2G12A mutant polypeptides can but need not comprise an amino-terminal methionine, which may be introduced by engineering or as a result of a bacterial expression process.

In various embodiments, a PLA2G12A mutant polypeptide comprises an amino acid sequence that is at least about 85 percent identical to a sequence selected from SEQ ID NOs:9, 11, 13, 15, 17, 19, 21, 23, 25, 27. In other embodiments, a PLA2G12A mutant polypeptide comprises an amino acid sequence that is at least about 90 percent, or about 95, 96, 97, 98, or 99 percent identical to a sequence selected from SEQ ID NOs:9, 11, 13, 15, 17, 19, 21, 23, 25, 27. Such PLA2G12A mutant polypeptides preferably, but need not, possess at least one activity of a PLA2G12A mutant polypeptide, such as the ability to lower blood glucose, insulin, triglyceride, or cholesterol levels; the ability to reduce body weight; or the ability to improve glucose tolerance or insulin sensitivity. The present invention also encompasses nucleic acid molecules encoding such PLA2G12A mutant polypeptide sequences.

In some instances, the PLA2G12A polypeptide used to treat or ameliorate a metabolic disorder in a subject is a mature form of a PLA2G12A polypeptide from the same species as the subject. Likewise, in some instances, the PLA2G12A mutant polypeptide used to treat or ameliorate a metabolic disorder in a subject is derived from a mature form of a PLA2G12A polypeptide of the same species as the subject.

A PLA2G12A polypeptide or PLA2G12A mutant polypeptide is preferably biologically active. In various respective embodiments, a PLA2G12A polypeptide or a PLA2G12A mutant polypeptide has a biological activity that is equivalent to, greater to or less than that of the naturally occurring form of the mature PLA2G12A polypeptide from which the signal peptide has been removed. Examples of biological activities include the ability to lower blood glucose, insulin, triglyceride, or cholesterol levels; the ability to reduce body weight; or the ability to improve glucose tolerance, lipid tolerance, or insulin sensitivity, the ability to lower urine glucose and protein excretion. In some embodiments, the PLA2G12A mutant polypeptide lacks phospholipase activity, but is biologically active.

In some embodiments, a PLA2G12A polypeptide or a PLA2G12A mutant polypeptide described herein further comprise a half life-extending moiety that increases the serum half-life of the polypeptide in a mammal compared to the serum half-life of the polypeptide lacking the half life-extending moiety in a mammal. For example, the half life-extending moiety is one or more of: polyethylene glycol (PEG), human serum albumin (HSA), an immunoglobulin (IgG), and an Fc moiety.

A "conservative amino acid substitution" can involve a substitution of a native amino acid residue (i.e., a residue found in a given position of the wild-type PLA2G12A polypeptide sequence) with a non-native residue (i.e., a residue that is not found in a given position of the wild-type PLA2G12A polypeptide sequence) such that there is little or no effect on the polarity or charge of the amino acid residue at that position. Conservative amino acid substitutions also encompass non-naturally occurring amino acid residues (as defined herein) that are typically incorporated by chemical peptide synthesis rather than by synthesis in biological systems. These include peptidomimetics, and other reversed or inverted forms of amino acid moieties.

Naturally occurring residues can be divided into classes based on common side chain properties:
 (1) hydrophobic: norleucine, Met, Ala, Val, Leu, Ile;
 (2) neutral hydrophilic: Cys, Ser, Thr;
 (3) acidic: Asp, Glu;
 (4) basic: Asn, Gln, His, Lys, Arg;
 (5) residues that influence chain orientation: Gly, Pro; and
 (6) aromatic: Trp, Tyr, Phe.

Additional groups of amino acids can also be formulated using the principles described in, e.g., Creighton (1984) PROTEINS: STRUCTLRE AND MOLECULAR PROPERTIES (2d Ed. 1993), W.H. Freeman and Company. In some instances it can be useful to further characterize substitutions based on two or more of such features (e.g., substitution with a "small polar" residue, such as a Thr residue, can represent a highly conservative substitution in an appropriate context).

Conservative substitutions can involve the exchange of a member of one of these classes for another member of the same class. Non-conservative substitutions can involve the exchange of a member of one of these classes for a member from another class.

Synthetic, rare, or modified amino acid residues having known similar physiochemical properties to those of an above-described grouping can be used as a "conservative" substitute for a particular amino acid residue in a sequence. For example, a D-Arg residue may serve as a substitute for a typical L-Arg residue. It also can be the case that a particular substitution can be described in terms of two or more of the above described classes (e.g., a substitution with a small and hydrophobic residue means substituting one amino acid with a residue(s) that is found in both of the above-described classes or other synthetic, rare, or modified residues that are known in the art to have similar physiochemical properties to such residues meeting both definitions).

The terms "therapeutically effective dose" and "therapeutically effective amount," as used herein, means an amount of PLA2G12A peptide or PLA2G12A mutant polypeptide that elicits a biological or medicinal response in a tissue system, animal, or human being sought by a researcher, physician, or other clinician, which includes alleviation or amelioration of the symptoms of the disease or disorder being treated, i.e., an amount of PLA2G12A polypeptide or PLA2G12A mutant polypeptide that supports an observable level of one or more desired biological or medicinal response, for example lowering blood glucose, insulin, triglyceride, or cholesterol levels; reducing body weight; reducing fat mass, or improving glucose tolerance, or insulin sensitivity, as well as slowing down the progression of such conditions.

II. PLA2G12A POLYPEPTIDES AND PLA2G12A MUTANT POLYPEPTIDES

The present inventors have found that adeno-associated virus (AAV)-mediated over-expression of PLA2G12A polypeptide in a diet-induced obesity (DIO) animal model resulted, inter alia, in lowered body weight (despite increased food intake), improved glucose tolerance, improved insulin tolerance, lower blood glucose, lower serum insulin, lower triglyceride levels, and lower fat mass in these animals ("PLA2G12A animals") compared to controls. See Example 2. This confirmed their hypothesis that PLA2G12A polypeptide is a metabolic regulator and can be used therapeutically for the treatment of a metabolic disorder, such as type 2 diabetes, dyslipidemia, insulin resistance, metabolic syndrome, obesity and/or diabetic nephropathy.

In further work, the present inventors replaced the histidine residue at position 110 in SEQ ID NO:1 (H110) with a lysine residue. Because H110 is part of the His-Asp catalytic dyad, this substitution was expected to eliminate the phospholipase activity of the resulting PLA2G12A mutant polypeptide (PLA2G12A-H110L). However, the present inventors surprisingly found that AAV-mediated over-expression of PLA2G12A-H110L in the DIO animal model resulted, inter alia, in decreased body weight, improved glucose tolerance, lower serum insulin levels and lower blood glucose levels in these animals ("PLA2G12A-H110L animals") compared to controls, and even compared to PLA2G12A animals. See Example 3. Thus, the PLA2G12A mutant polypeptides of the invention, such as PLA2G12A-H110L, also can be used therapeutically for the treatment of a metabolic disorder, such as obesity, diabetes and/or dyslipidemia. In fact, PLA2G12A-H110L was superior to wild-type PLA2G12A with respect to decreased body weight, improved glucose tolerance, lower serum insulin levels and lower blood glucose levels.

A. PLA2G12A Polypeptides and Nucleic Acids

In various examples, a nucleic acid sequence encoding a PLA2G12A polypeptide, which can comprise all or a portion of SEQ ID NOs: 1 and 2, can be isolated and/or amplified from genomic DNA, or cDNA using appropriate oligonucleotide primers. Primers can be designed based on the nucleic and amino acid sequences provided herein according to standard (RT)-PCR amplification techniques. The amplified nucleic acid can then be cloned into a suitable vector and characterized by DNA sequence analysis.

Oligonucleotides for use as probes in isolating or amplifying all or a portion of the sequences provided herein can be designed and generated using standard synthetic techniques, e.g., automated DNA synthesis apparatus, or can be isolated form a longer sequence of DNA.

In vivo, PLA2G12A is expressed as a continuous amino acid sequence comprising a predicted signal sequence. The 189 amino acid sequence of full-length human PLA2G12A is (shown with predicted cleaved signal sequence underlined):

(SEQ ID NO: 1)
MALLSRPALTLLLLLMAAVVRCQEQAQTTDWRATLKTIRNGVHKIDT
YLNAALDLLGGEDGLCQYKCSDGSKPFPRYGYKPSPPNCGSPLFGV
HLNIGIPSLTKCCNQHDRCYETCGKSKNDCDEEFQYCLSKICRDVQK
TLGLTQHVQACETTVELLFDSVIHLGCKPYLDSQRAACRCHYEEKTDL and is encoded by the DNA sequence (shown with optional stop codon):

(SEQ ID NO: 2)
atggccctgctctcgcgccccgcgctcaccctcctgctcctcctcat
ggccgctgttgtcaggtgccaggagcaggcccagaccaccgactgga
gagccaccctgaagaccatccggaacggcgttcataagatagacacg
tacctgaacgccgccttggacctcctgggaggcgaggacggtctctg
ccagtataaatgcagtgaccggatctaagcctttcccacgttatggtt
ataaaccctccccaccgaatggatgtggctctccactgtttggtgtt
catcttaacattggtatcccttccctgacaaagtgttgcaaccaaca
cgacaggtgctatgagacctgtggcaaaagcaagaatgactgtgatg
aagaattccagtattgcctctccaagatctgccgagatgtacagaaa
acactaggactaactcagcatgttcaggcatgtgaaacaacagtgga
gctcttgtttgacagtgttatacatttaggttgtaaaccatatctgg
acagccaacgagccgcatgcaggtgtcattatgaagaaaaactgat
ctttaa.

The 167 amino acid sequence of human PLA2G12A following cleavage of the predicted 22 amino acid residue signal sequence is:

(SEQ ID NO: 3)
QEQAQTTDWRATLKTIRNGVHKIDTYLNAALDLLGGEDGLCQYKCSD
GSKPFPRYGYKPSPPNCGSPLFGVHLNIGIPSLTKCCNQHDRCYET
CGKSKNDCDEEFQYCLSKICRDVQKTLGLTQHVQACETTVELLFDSV
IHLGCKPYLDSQRAACRCHYEEKTDL and is encoded by the DNA sequence (shown with optional stop codon):

(SEQ ID NO: 4)
caggagcaggcccagaccaccgactggagagccaccctgaagaccat
ccggaacggcgttcataagatagacacgtacctgaacgccgccttgg
acctcctgggaggcgaggacggtctctgccagtataaatgcagtgac
ggatctaagcctttcccacgttatggttataaaccctccccaccgaa
tggatgtggctctccactgtttggtgttcatcttaacattggtatcc
cttccctgacaaagtgttgcaaccaacacgacaggtgctatgagacc
tgtggcaaaagcaagaatgactgtgatagaagaattccagtattgcct
ctccaagatctgccgagatgtacagaaaacactaggactaactcagc atgttcaggcatgtgaaacaacagtggagctcttgtttgacagtgtt
atacatttaggttgtaaaccatatctggacagccaacgagccgcatg
caggtgtcattatgaagaaaaactgatctttaa.

The 192 amino acid sequence of full length murine PLA2G12A is (shown with predicted cleaved signal sequence underlined):

(SEQ ID NO: 5)
MVTPRPAPARSPPALLLLLLLATARGQEQDQTTDWRATLKTIRNGIHK
IDTYLNAALDLLGGEDGLCQYKCSDGSKPVPRYGYKPSPPNGCGSPL
FGVHLNIGIPSLTKCCNQHDRCYETCGKSKNDCDEEFQYCLSKICRD
VQKTLGLSQNVQACETTVELLFDSVIHLGCKPYLDSQRAACWCRYEE
KTDL and is encoded by the DNA sequence (shown with optional stop codon):

(SEQ ID NO: 6)
atggtgactccgcggcccgcgcccgcccggagccccgcgctcctcct
cctcctgctgctggccactgcgcgtgggcaggaacaggaccagacca
ccgactggagggccaccctcaagaccatccgcaacggcatccacaag
atagacacgtacctcaacgcgcgctggacctgctgggcggggagga
cgggctctgccagtacaagtgcagcgacggatcgaagcctgttccac
gctatggatataaaccatctccaccaaatggctgtggctcgccactg
tttggcgttcatctgaacataggtatcccttccctgaccaagtgctg
caaccagcacgacagatgctacgagacctgcgggaaaagcaagaacg
actgtgacgaggagttccagtactgcctctccaagatctgcagagac
gtgcagaagacgctcggactatctcagaacgtccaggcatgtgagac
aacggtagagctcctcttttgacagcgtcatccatttaggctgcaagc
catacctggacagccagcgggctgcatgctggtgtcgttatgaagaa
aaaacagatctataa.

The 167 amino acid sequence of murine PLA2G12A following cleavage of the predicted 25 amino acid residue signal sequence is:

(SEQ ID NO: 7)
QEQDQTTDWRATLKTIRNGIHKIDTYLNAALDLLGGEDGLCQYKCSD
GSKPVPRYGYKPSPPNGCGSPLFGVHLNIGIPSLTKCCNQHDRCYET
CGKSKNDCDEEFQYCLSKICRDVQKTLGLSQNVQACETTVELLFDSV
IHLGCKPYLDSQRAACWCRYEEKTDL and is encoded by the DNA sequence (shown with optional stop codon):

B. PLA2G12A Mutant Polypeptides and Nucleic Acids (SEQ ID NO: 8)
caggaacaggaccagaccaccgactggagggaccaccctcaagaccat
ccgcaacggcatccacaagatagacacgtacctcaacgccgcgctgg -continued
```
acctgctgggcgggaggacgggctctgccagtacaagtgcagcgac ggatcgaagcctgttccacgctatggatataaaccatctccaccaaa tggctgtggctcgccactgtttggcgttcatctgaacataggtatcc cttccctgaccaagtgctgcaaccagcacgacagatgctacgagacc tgcgggaaaagcaagaacgactgtaacgaggagttccagtactgcct ctccaagatctgcagagacgtgcagaagacgctcggactatctcaga acgtccaggcatgtgagacaacggtggagctcctctttgacagcgtc atccatttaggctgcaagccatacctggacagccagcgggctgcatg ctggtgtcgttatgaagaaaaaacagatctataa.
```

As disclosed herein, a PLA2G12A mutant polypeptide can be engineered and/or produced using standard molecular biology methodology. As with the PLA2G12A polypeptides described above, a nucleic sequence encoding a PLA2G12A mutant polypeptide can be amplified from cDNA using appropriate oligonucleotide primers. Primers can be designed based on the nucleic and amino acid sequences provided herein according to standard (RT)-PCR amplification techniques. The amplified nucleic acid can then be cloned into a suitable vector and characterized by DNA sequence analysis.

Oligonucleotides for use as probes in isolating or amplifying all or a portion of the sequences provided herein can be designed and generated using standard synthetic techniques, e.g., automated DNA synthesis apparatus, or can be isolated form a longer sequence of DNA.

Nucleic acid sequences encoding a PLA2G12A mutant polypeptide provided herein, including those degenerate to SEQ ID NOs: 10, 12, 14, 16, 18, 20, 22, 24, 26 and 28 form other aspects of the instant disclosure.

In one embodiment, the PLA2G12A mutant polypeptide comprises an amino acid residue substitution at position H110 in SEQ ID NO: 1. For example, the amino acid sequence of full length human PLA2G12A with an H110L mutation is (shown with predicted cleaved signal sequence underlined):

(SEQ ID NO: 9)
MALLSRRALTLLLLLMAAVVRCQEQAQTTDWRATLKTIPNGVHKIDT

YLNAALDLLGGFDGLCQYKCSDGSKPFPRYGYKPSPPNGCGSPLFGV

HLNIGIPSLTKCCNQLDRCYETCGKSKNDCDEEFQYCLSKICRDVQK

TLGLTQHVQACETTVELLFDSVIHLGCKPYLDSQRAACRCHYEEKTDL which is encoded by the DNA sequence:

(SEQ ID NO: 10)
```
atggccctgctctcgcgccccgcgctcaccctcctgctcctcctcat ggccgctgttgtcaggtgccaggagcaggcccagaccaccgactgga gagccaccctgaagaccatccggaacggcgttcataagatagacacg tacctgaacgccgccttggacctcctgggaggcgaggacggtctctg ccagtataaatgcagtgacggatctaagcctttcccacgttatggtt ataaaccctccccaccgaatgatgtggctctccactgtttggtgtt catcttaacattggtatccttccctgacaaagtgttgcaaccaact
```

-continued
```
cgacaggtgctatgagacctgtggcaaaagcaagaatgactgtgatg aagaattccagtattgcctctccaagatctgccgagatgtacagaaa acactaggactaactcagcatgttcaggcatgtgaaacaacagtgga gctcttgtttgacagtgttatacatttaggttgtaaaccatatctgg acagccaacgagccgcatgcaggtgtcattatgaagaaaaaactgat ctttaa.
```

In a related embodiment, the PLA2G12A mutant polypeptide comprises the amino acid sequence of SEQ ID NO:9 from which the predicted 22 amino acid signal sequence has been cleaved:

(SEQ ID NO: 11)
QEQAQTTDWRATLKTIRNGVHKIDTYLNAALDLLGGEDGLCQYKCSD

GSKPFPRYGYKPSPPNGCGSPLFGVHLNIGIPSLTKCCNQLDRCYET

CGKSKNDCDEEFQYCLSKICRDVQKTLGLTQHVQACETTVELLFDSV

IHLGCKPYLDSQRAACRCHYEEKTDL which is encoded by the DNA sequence:

(SEQ ID NO: 12)
```
caggagcaggcccagaccaccgactggagagccaccctgaagaccat ccggaacggcgttcataagatagacacgtacctgaacgccgccttgg acctcctgggaggcgaggacggtctctgccagtataaatgcagtgac ggatctaagcctttcccacgttatggttataaaccctccccaccgaa tggatgtggctctccactgtttggtgttcatcttaacattggtatcc cttccctgacaaagtgttgcaaccaactcgacaggtgctatgagacc tgtggcaaaagcaagaatgactgtgatgaagaattccagtattgcct ctccaagatctgccgagatgtacagaaaacactaggactaactcagc atgttcaggcatgtgaaacaacagtggagctcttgtttgacagtgtt atacatttaggttgtaaaccatatctggacagccaacgagccgcatg caggtgtcattatgaagaaaaaactgatctttaa.
```

In another embodiment, the PLA2G12A mutant polypeptide comprises the amino acid sequence of full length human PLA2G12A (SEQ ID NO:1) with an H110M mutation is (shown with predicted cleaved signal sequence underlined):

(SEQ ID NO: 13)
MALLSRPALTLLLLLMAAVVRCQEQAQTTDWRATLKTIRNGVHKIDT

YLNAALDLLGGEDGLCQYKCSDGSKPFPRYGYKPSPPNGCGSPLFGV

HLNIGIPSLTKCCNQMDRCYETCGKSKNDCDEEFQYCLSKICRDVQK

TLGLTQHVQACETTVELLFDSVIHLGCKPYLDSQRAACRCHYEEKTDL which is encoded by the DNA sequence:

(SEQ ID NO: 14)
```
atggccctgctctcgcgccccgcgctcaccctcctgctcctcctcat ggccgctgttgtcaggtgccaggagcaggcccagaccaccgactgga gagccaccctgaagaccatccggaacggcgttcataagatagacacg
```

```
tacctgaacgccgccttggacctcctgggaggcgaggacggtctctg ccagtataaatgcagtgacggatctaagcctttcccacgttatggtt ataaaccctccccaccgaatggatgtggctctccactgtttggtgtt catcttaacattggtatcccttccctgacaaagtgttgcaaccaaat ggacaggtgctatgagacctgtggcaaaagcaagaatgactgtgatg aagaattccagtattgcctctccaagatctgccgagatgtacagaaa acactaggactaactcagcatgttcaggcatgtgaaacaacagtgga gctcttgtttgacagtgttatacatttaggttgtaaaccatatctgg acagccaacgagccgcatgcaggtgtcattatgaagaaaaaactgat ctttaa.
```

In a related embodiment, the PLA2G12A mutant polypeptide comprises the amino acid sequence of SEQ ID NO: 13 from which the predicted 22 amino acid signal sequence has been cleaved:

(SEQ ID NO: 15)
```
QEQAQTTDWRATLKTIRNGVHKIDTYLNAALDLLGGEDGLCQYKCSD

GSKPFPRYGYKPSPPNGCGSPLFGVHLNIGIPSLTKCCNQMDRCYET

CGKSKNDCDEEFQYCLSKICRDVQKTLGLTQHVQACETTVELLFDSV

IHLGCKPYLDSQRAACRCHYEEKTDL
``` which is encoded by the DNA sequence:

(SEQ ID NO: 16)
```
caggagcaggcccagaccaccgactggagagccaccctgaagaccat ccggaacggcgttcataagatagacacgtacctgaacgccgccttgg acctcctgggaggcgaggacggtctctgccagtataaatgcagtgac ggatctaagcctttcccacgttatggttataaaccctccccaccgaa tggatgtggctctccactgtttggtgttcatcttaacattggtatcc cttccctgacaaagtgttgcaaccaaatggacaggtgctatgagacc tgtggcaaaagcaagaatgactgtgatgaagaattccagtattgcct ctccaagatctgccgagatgtacagaaaacactaggactaactcagc atgttcaggcatgtgaaacaacagtggagctcttgtttgacagtgtt atacatttaggttgtaaaccatatctggacagccaacgagccgcatg caggtgtcattatgaagaaaaaactgatctttaa.
```

In another embodiment, the PLA2G12A mutant polypeptide comprises the amino acid sequence of full length human PLA2G12A (SEQ ID NO: 1) with an H110A mutation is (shown with predicted cleaved signal sequence underlined):

(SEQ ID NO: 17)
MALLSRPALTLLLLLMAAVVRCQEQAQTTDWRATLKTIRNGVHKIDT

YLNAALDLLGGEDGLCQYKCSDGSKPFPRYGYKPSPPNGCGSPLFGV

HLNIGIPSLTKCCNQADRCYETCGKSKNDCDEEFQYCLSKICRDVQK

TLGLTQHVQACETTVELLFDSVIHLGCKPYLDSQRAACRCHYEEKTD

L which is encoded by the DNA sequence:

(SEQ ID NO: 18)
```
atggccctgctctcgcgccccgcgctcaccctcctgctcctcctcat ggccgctgttgtcaggtgccaggagcaggcccagaccaccgactgga gagccaccctgaagaccatccggaacggcgttcataagatagacacg tacctgaacgccgccttggacctcctgggaggcgaggacggtctctg ccagtataaatgcagtgacggatctaagcctttcccacgttatggtt ataaaccctccccaccgaatggatgtggctctccactgtttggtgtt catcttaacattggtatcccttccctgacaaagtgttgcaaccaagc cgacaggtgctatgagacctgtggcaaaagcaagaatgactgtgatg aagaattccagtattgcctctccaagatctgccgagatgtacagaaa acactaggactaactcagcatgttcaggcatgtgaaacaacagtgga gctcttgtttgacagtgttatacatttaggttgtaaaccatatctgg acagccaacgagccgcatgcaggtgtcattatgaagaaaaaactgat ctttaa.
```

In a related embodiment, the PLA2G12A mutant polypeptide comprises the amino acid sequence of SEQ ID NO: 17 from which the predicted 22 amino acid signal sequence has been cleaved:

(SEQ ID NO: 19)
```
QEQAQTTDWRATLKTIRNGVHKIDTYLNAALDLLGGEDGLCQYKCSD

GSKPFPRYGYKPSPPNGCGSPLFGVHLNIGIPSLTKCCNQADRCYET

CGKSKNDCDEEFQYCLSKICRDVQKTLGLTQHVQACETTVELLFDSV

IHLGCKPYLDSQRAACRCHYEEKTDL
``` which is encoded by the DNA sequence:

(SEQ ID NO: 20)
```
caggagcaggcccagaccaccgactggagagccaccctgaagaccat ccggaacggcgttcataagatagacacgtacctgaacgccgccttgg acctcctgggaggcgaggacggtctctgccagtataaatgcagtgac ggatctaagcctttcccacgttatggttataaaccctccccaccgaa tggatgtggctctccactgtttggtgttcatcttaacattggtatcc cttccctgacaaagtgttgcaaccaagccgacaggtgctatgagacc tgtggcaaaagcaagaatgactgtgatgaagaattccagtattgcct ctccaagatctgccgagatgtacagaaaacactaggactaactcagc atgttcaggcatgtgaaacaacagtggagctcttgtttgacagtgtt atacatttaggttgtaaaccatatctggacagccaacgagccgcatg caggtgtcattatgaagaaaaaactgatctttaa.
```

In another embodiment, the PLA2G12A mutant polypeptide comprises the amino acid sequence of full length human PLA2G12A (SEQ ID NO: 1) with an H110V mutation is (shown with predicted cleaved signal sequence underlined):

(SEQ ID NO: 21)
MALLSRPALTLLLLLMAAVVRCQEQAQTTDWRATLKTIRNGVHKIDTY

LNAALDLLGGEDGLCQYKCSDGSKPFPRYGYKPSPPNGCGSPLFGVH

-continued
LNIGIPSLTKCCNQVDRCYETCGKSKNDCDEEFQYCLSKICRDVQKT

LGLTQHVQACETTVELLFDSVIHLGCKPYLDSQRAACRCHYEEKTDL which is encoded by the DNA sequence:

(SEQ ID NO: 22)
atggccctgctctcgcgccccgcgctcaccctcctgctcctcctcat ggccgctgttgtcaggtgccaggagcaggcccagaccaccgactgga gagccaccctgaagaccatccggaacggcgttcataagatagacacg tacctgaacgccgccttggacctcctgggaggcgaggacggtctctg ccagtataaatgcagtgacggatctaagcctttcccacgttatggtt ataaaccctccccaccgaatggatgtggctctccactgtttggtgtt catcttaacattggtatcccttccctgacaaagtgttgcaaccaagt tgacaggtgctatgagacctgtggcaaaagcaagaatgactgtgatg aagaattccagtattgcctctccaagatctgccgagatgtacagaaa acactaggactaactcagcatgttcaggcatgtgaaacaacagtgga gctcttgtttgacagtgttatacatttaggttgtaaaccatatctgg acagccaacgagccgcatgcaggtgtcattatgaagaaaaaactgat ctttaa.

In a related embodiment, the PLA2G12A mutant polypeptide comprises the amino acid sequence of SEQ ID NO:21 from which the predicted 22 amino acid signal sequence has been cleaved:

(SEQ ID NO: 23)
QEQAQTTDWRATLKTIRNGVHKIDTYLNAALDLLGGEDGLCQYKCSD

GSKPFPRYGYKPSPPNGCGSPLFGVHLNIGIPSLTKCCNQVDRCYET

CGKSKNDCDEEFQYCLSKICRDVQKTLGLTQHVQACETTVELLFDSV

IHLGCKPYLDSQRAACRCHYEEKTDL which is encoded by the DNA sequence:

(SEQ ID NO: 24)
caggagcaggcccagaccaccgactggagagccaccctgaagaccat ccggaacggcgttcataagatagacacgtacctgaacgccgccttgg acctcctgggaggcgaggacggtctctgccagtataaatgcagtgac ggatctaagcctttcccacgttatggttataaaccctccccaccgaa tggatgtggctctccactgtttggtgttcatcttaacattggtatcc cttccctgacaaagtgttgcaaccaagttgacaggtgctatgagacc tgtggcaaaagcaagaatgactgtgatgaagaattccagtattgcct ctccaagatctgccgagatgtacagaaaacactaggactaactcagc atgttcaggcatgtgaaacaacagtggagctcttgtttgacagtgtt atacatttaggttgtaaaccatatctggacagccaacgagccgcatg caggtgtcattatgaagaaaaaactgatctttaa.

In another embodiment, the PLA2G12A mutant polypeptide comprises the amino acid sequence of full length human PLA2G12A (SEQ ID NO: 1) with an H110I mutation is (shown with predicted cleaved signal sequence underlined):

(SEQ ID NO: 25)
MALLSRPALTLLLLLMAAVVRCQEQAQTTDWRATLKTIRNGVHKIDT

YLNAALDLLGGEDGLCQYKCSDGSKPFPRYGYKPSPPNGCGSPLFGV

HLNIGIPSLTKCCNQIDRCYETCGKSKNDCDEEFQYCLSKICRDVQK

TLGLTQHVQACETTVELLFDSVIHLGCKPYLDSQRAACRCHYEEKTD

L which is encoded by the DNA sequence:

(SEQ ID NO: 26)
atggccctgctctcgcgccccgcgctcaccctcctgctcctcctcat ggccgctgttgtcaggtgccaggagcaggcccagaccaccgactgga gagccaccctgaagaccatccggaacggcgttcataagatagacacg tacctgaacgccgccttggacctcctgggaggcgaggacggtctctg ccagtataaatgcagtgacggatctaagcctttcccacgttatggtt ataaaccctccccaccgaatggatgtggctctccactgtttggtgtt catcttaacattggtatcccttccctgacaaagtgttgcaaccaaat cgacaggtgctatgagacctgtggcaaaagcaagaatgactgtgatg aagaattccagtattgcctctccaagatctgccgagatgtacagaaa acactaggactaactcagcatgttcaggcatgtgaaacaacagtgga gctcttgtttgacagtgttatacatttaggttgtaaaccatatctgg acagccaacgagccgcatgcaggtgtcattatgaagaaaaaactgat ctttaa.

In a related embodiment, the PLA2G12A mutant polypeptide comprises the amino acid sequence of SEQ ID NO:25 from which the predicted 22 amino acid signal sequence has been cleaved:

(SEQ ID NO: 27)
QEQAQTTDWRATLKTIRNGVHKIDTYLNAALDLLGGEDGLCQYKCSD

GSKPFPRYGYKPSPPNGCGSPLFGVHLNIGIPSLTKCCNQIDRCYET

CGKSKNDCDEEFQYCLSKICRDVQKTLGLTQHVQACETTVELLFDSV

IHLGCKPYLDSQRAACRCHYEEKTDL which is encoded by the DNA sequence:

(SEQ ID NO: 28)
caggagcaggcccagaccaccgactggagagccaccctgaagaccat ccggaacggcgttcataagatagacacgtacctgaacgccgccttgg acctcctgggaggcgaggacggtctctgccagtataaatgcagtgac ggatctaagcctttcccacgttatggttataaaccctccccaccgaa tggatgtggctctccactgtttggtgttcatcttaacattggtatcc cttccctgacaaagtgttgcaaccaaatcgacaggtgctatgagacc tgtggcaaaagcaagaatgactgtgatgaagaattccagtattgcct ctccaagatctgccgagatgtacagaaaacactaggactaactcagc -continued

```
atgttcaggcatgtgaaacaacagtggagctcttgtttgacagtgtt atacatttaggttgtaaaccatatctggacagccaacgagccgcatg caggtgtcattatgaagaaaaaactgatctttaa.
```

C. Vectors

In order to express the nucleic acid sequences provided herein, the appropriate coding sequences, e.g., SEQ ID NOs:2, 4, 6, or 8, can be cloned into a suitable vector and after introduction in a suitable host, the sequence can be expressed to produce the encoded polypeptide according to standard cloning and expression techniques, which are known in the art (e.g., as described in Sambrook, J., Fritsh, E. F., and Maniatis, T. Molecular Cloning: A Laboratory Manual 2nd, ed., Cold Spring Harbor Laboratory, Cold Spring Harbor Laboratory Press. Cold Spring Harbor, N.Y., 1989). The invention also relates to such vectors comprising a nucleic acid sequence according to the invention.

A "vector" refers to a delivery vehicle that (a) promotes the expression of a polypeptide-encoding nucleic acid sequence: (b) promotes the production of the polypeptide therefrom; (c) promotes the transfection/transformation of target cells therewith; (d) promotes the replication of the nucleic acid sequence, (e) promotes stability of the nucleic acid; (f) promotes detection of the nucleic acid and/or transformed/transfected cells; and/or (g) otherwise imparts advantageous biological and/or physiochemical function to the polypeptide-encoding nucleic acid. A vector can be any suitable vector, including chromosomal, non-chromosomal, and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors derived from combinations of plasmids and phage DNA, and viral nucleic acid (RNA or DNA) vectors.

A recombinant expression vector can be designed for expression of a PLA2G12A polypeptide in prokaryotic (e.g., *E. coli*) or eukaryotic cells (e.g., insect cells, using baculovirus expression vectors, yeast cells, or mammalian cells). Representative host cells include those hosts typically used for cloning and expression, including *Escherichia coli* strains TOP10F', TOP10, DH10B, DH5a, HB101, W3110, BL21(DE3) and BL21 (DE3)pLysS, BLUESCRIPT (Stratagene), mammalian cell lines CHO. CHO-K1, HEK293, 293-EBNA pIN vectors (Van Heeke & Schuster, *J. Biol. Chem.* 264: 5503-5509 (1989); pET vectors (Novagen, Madison Wis.). Alternatively, the recombinant expression vector can be transcribed and translated in vitro, for example using T7 promoter regulatory sequences and T7 polymerase and an in vitro translation system. Preferably, the vector contains a promoter upstream of the cloning site containing the nucleic acid sequence encoding the polypeptide. Examples of promoters, which can be switched on and off, include the lac promoter, the T7 promoter, the trc promoter, the tac promoter and the trp promoter.

Thus, provided herein are vectors comprising a nucleic acid sequence encoding PLA2G12A polypeptides or PLA2G12A mutant polypeptides that facilitate the expression of recombinant PLA2G12A or mutant PLA2G12A. In various embodiments, the vectors comprise an operably linked nucleotide sequence which regulates the expression of PLA2G12A or mutant PLA2G12A. A vector can comprise or be associated with any suitable promoter, enhancer, and other expression-facilitating elements. Examples of such elements include strong expression promoters (e.g., a human CMV IE promoter/enhancer, an RSV promoter, SV40 promoter, SL3-3 promoter, MMTV promoter, or HIV LTR promoter, EF1alpha promoter, CAG promoter), effective poly (A) termination sequences, an origin of replication for plasmid product in *E. coli*, an antibiotic resistance gene as a selectable marker, and/or a convenient cloning site (e.g., a polylinker). Vectors also can comprise an inducible promoter as opposed to a constitutive promoter such as CMV IE. In one aspect, a nucleic acid comprising a sequence encoding a PLA2G12A polypeptide or PLA2G12A mutant polypeptide which is operatively linked to a tissue specific promoter which promotes expression of the sequence in a metabolically-relevant tissue, such as liver or pancreatic tissue is provided.

D. Host Cells

In another aspect of the instant disclosure, host cells comprising the nucleic acids and vectors disclosed herein are provided. In various embodiments, the vector or nucleic acid is integrated into the host cell genome, which in other embodiments the vector or nucleic acid is extra-chromosomal.

Recombinant cells, such as yeast, bacterial (e.g., *E. coli*), and mammalian cells (e.g., immortalized mammalian cells) comprising such a nucleic acid, vector, or combinations of either or both thereof are provided. In various embodiments cells comprising a non-integrated nucleic acid, such as a plasmid, cosmid, phagemid, or linear expression element, which comprises a sequence coding for expression of a PLA2G12A polypeptide or PLA2G12A mutant polypeptide, are provided.

A vector comprising a nucleic acid sequence encoding a PLA2G12A polypeptide or PLA2G12A mutant polypeptide provided herein can be introduced into a host cell by transformation or by transfection. Methods of transforming a cell with an expression vector are well known.

A PLA2G12A or mutant PLA2G12A-encoding nucleic acid can be positioned in and/or delivered to a host cell or host animal via a viral vector. Any suitable viral vector can be used in this capacity. A viral vector can comprise any number of viral polynucleotides, alone or in combination with one or more viral proteins, which facilitate delivery, replication, and/or expression of the nucleic acid of the invention in a desired host cell. The viral vector can be a polynucleotide comprising all or part of a viral genome, a viral protein/nucleic acid conjugate, a virus-like particle (VLP), or an intact virus particle comprising viral nucleic acids and a PLA2G12A polypeptide or PLA2G12A mutant polypeptide-encoding nucleic acid. A viral particle viral vector can comprise a wild-type viral particle or a modified viral particle. The viral vector can be a vector which requires the presence of another vector or wild-type virus for replication and/or expression (e.g., a viral vector can be a helper-dependent virus), such as an adenoviral vector amplicon. Typically, such viral vectors consist of a wild-type viral particle, or a viral particle modified in its protein and/or nucleic acid content to increase transgene capacity or aid in transfection and/or expression of the nucleic acid (examples of such vectors include the herpes virus/AAV amplicons). Typically, a viral vector is similar to and/or derived from a virus that normally infects humans. Suitable viral vector particles in this respect, include, for example, adenoviral vector particles (including any virus of or derived from a virus of the adenoviridae), adeno-associated viral vector particles (AAV vector particles) or other parvoviruses and parvoviral vector particles, papillomaviral vector particles, flaviviral vectors, alphaviral vectors, herpes viral vectors, pox virus vectors, retroviral vectors, including lentiviral vectors.

E. Isolation of a PLA2G12A Polypeptide

A PLA2G12A polypeptide or PLA2G12A mutant polypeptide expressed as described herein can be isolated using standard protein purification methods. A PLA2G12A polypeptide or PLA2G12A mutant polypeptide can be isolated from a cell in which is it naturally expressed or it can be isolated from a cell that has been engineered to express PLA2G12A or mutant PLA2G12A, for example, a cell that does not naturally express PLA2G12A.

Protein purification methods that can be employed to isolate a PLA2G12A polypeptide or PLA2G12A mutant polypeptide, as well as associated materials and reagents, are known in the art. Exemplary methods of purifying a PLA2G12A polypeptide or PLA2G12A mutant polypeptide are provided in the Examples herein below. Additional purification methods that may be useful for isolating a PLA2G12A polypeptide or PLA2G12A mutant polypeptide can be found in references such as Bootcov M R. 1997, *Proc. Natl. Acad. Sci. USA* 94:11514-9, Fairlie W D, 2000, *Gene* 254: 67-76.

III. PHARMACEUTICAL COMPOSITIONS

Pharmaceutical compositions comprising a PLA2G12A polypeptide or PLA2G12A mutant polypeptide are provided. Such PLA2G12A polypeptide pharmaceutical compositions can comprise a therapeutically effective amount of a PLA2G12A polypeptide in admixture with a pharmaceutically or physiologically acceptable formulation agent selected for suitability with the mode of administration. Likewise, such PLA2G12A mutant polypeptide pharmaceutical compositions can comprise a therapeutically effective amount of a PLA2G12A mutant polypeptide in admixture with a pharmaceutically or physiologically acceptable formulation agent selected for suitability with the mode of administration. The term "pharmaceutically acceptable carrier" or "physiologically acceptable carrier" as used herein refers to one or more formulation agents suitable for accomplishing or enhancing the delivery of a PLA2G12A polypeptide or PLA2G12A mutant polypeptide into the body of a human or non-human subject. The term includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In some cases it will be preferable to include isotonic agents, for example, sugars, polyalcohols such as mannitol, sorbitol, or sodium chloride in a pharmaceutical composition. Pharmaceutically acceptable substances such as wetting or minor amounts of auxiliary substances such as wetting or emulsifying agents, preservatives or buffers, which enhance the shelf life or effectiveness of the PLA2G12A polypeptide or PLA2G12A mutant polypeptide can also act as, or form a component of, a carrier. Acceptable pharmaceutically acceptable carriers are preferably nontoxic to recipients at the dosages and concentrations employed.

A pharmaceutical composition can contain formulation agent(s) for modifying, maintaining, or preserving, for example, the pH, osmolarity, viscosity, clarity, color, isotonicity, odor, sterility, stability, rate of dissolution or release, adsorption, or penetration of the composition. Suitable formulation agents include, but are not limited to, amino acids (such as glycine, glutamine, asparagine, arginine, or lysine), antimicrobials, antioxidants (such as ascorbic acid, sodium sulfite, or sodium hydrogen-sulfite), buffers (such as borate, bicarbonate, Tris-HCl, citrates, phosphates, or other organic acids), bulking agents (such as mannitol or glycine), chelating agents (such as ethylenediamine tetraacetic acid (EDTA)), complexing agents (such as caffeine, polyvinylpyrrolidone, beta-cyclodextrin, or hydroxypropyl-beta-cyclodextrin), fillers, monosaccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as Polysorbate 20 or Polysorbate 80; Triton; tromethamine; lecithin; cholesterol or tyloxapal), stability enhancing agents (such as sucrose or sorbitol), tonicity enhancing agents (such as alkali metal halides—preferably sodium or potassium chloride—or mannitol sorbitol), delivery vehicles, diluents, excipients and/or pharmaceutical adjuvants (see, e.g., REMINGTON: THE SCIENCE AND PRACTICE OF PHARMACY, 19th edition, (1995); Berge et al., J. Pharm. Sci., 6661), 1-19 (1977). Additional relevant principles, methods, and agents are described in, e.g., Lieberman et al., PHARMACEUTICAL DOSAGE FORMS-DISPERSE SYSTEMS (2nd ed., vol. 3, 1998); Ansel et al., PHARMACEUTICAL DOSAGE FORMS & DRUG DELIVERY SYSTEMS (7th ed. 2000); Martindale, THE EXTRA PHARMACOPEIA (31st edition), Remington's PHARMACEUTICAL SCIENCES (16th-20$^{th}$ and subsequent editions); The Pharmacological Basis Of Therapeutics, Goodman and Gilman, Eds. (9th ed.-1996); Wilson and Gisvolds' TEXTBOOK OF ORGANIC MEDICINAL AND PHARMACEUTICAL CHEMISTRY, Delgado and Remers, Eds. (10th ed., 1998). Principles of formulating pharmaceutically acceptable compositions also are described in, e.g., Aulton, PHARMACEUTICS: THE SCIENCE OF DOSAGE FORM DESIGN, Churchill Livingstone (New York) (1988), EXTEMPORANEOUS ORAL LIQUID DOSAGE PREPARATIONS, CSHP (1998), incorporated herein by reference for any purpose).

The optimal pharmaceutical composition will be determined by a skilled artisan depending upon, for example, the intended route of administration, delivery format, and desired dosage (see, e.g., Remington's PHARMACEUTICAL SCIENCES, supra). Such compositions can influence the physical state, stability, rate of in vivo release, and rate of in vivo clearance of a PLA2G12A polypeptide or PLA2G12A mutant polypeptide.

The primary vehicle or carrier in a pharmaceutical composition can be either aqueous or non-aqueous in nature. For example, a suitable vehicle or carrier for injection can be water, physiological saline solution, or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which can further include sorbitol or a suitable substitute. In one embodiment of the present invention, PLA2G12A polypeptide or PLA2G12A mutant polypeptide composition can be prepared for storage by mixing the selected composition having the desired degree of purity with optional formulation agents (Remington's PHARMACEUTICAL SCIENCES, supra) in the form of a lyophilized cake or an aqueous solution. Furthermore, the PLA2G12A polypeptide or PLA2G12A mutant polypeptide product can be formulated as a lyophilizate using appropriate excipients such as sucrose.

The PLA2G12A polypeptide or PLA2G12A mutant polypeptide pharmaceutical compositions can be selected for parenteral delivery. Alternatively, the compositions can be selected for inhalation or for delivery through the digestive tract, such as orally. The preparation of such pharmaceutically acceptable compositions is within the skill of the art.

The formulation components are present in concentrations that are acceptable to the site of administration. For example, buffers are used to maintain the composition at physiological pH or at a slightly lower pH, typically within a pH range of from about 5 to about 8.

When parenteral administration is contemplated, the therapeutic compositions for use in this invention can be in the form of a pyrogen-free, parenterally acceptable, aqueous solution comprising the desired PLA2G12A polypeptide or PLA2G12A mutant polypeptide in a pharmaceutically acceptable vehicle. A particularly suitable vehicle for parenteral injection is sterile distilled water in which a PLA2G12A polypeptide or PLA2G12A mutant polypeptide is formulated as a sterile, isotonic solution, properly preserved. Yet another preparation can involve the formulation of the desired molecule with an agent, such as injectable microspheres, bio-erodible particles, polymeric compounds (such as polylactic acid or polyglycolic acid), beads, or liposomes, that provides for the controlled or sustained release of the product which can then be delivered via a depot injection. Hyaluronic acid can also be used, and this can have the effect of promoting sustained duration in the circulation. Other suitable means for the introduction of the desired molecule include implantable drug delivery devices.

In one embodiment, a pharmaceutical composition can be formulated for inhalation. For example, a PLA2G12A polypeptide or PLA2G12A mutant polypeptide can be formulated as a dry powder for inhalation. PLA2G12A polypeptide or PLA2G12A mutant polypeptide inhalation solutions can also be formulated with a propellant for aerosol delivery. In yet another embodiment, solutions can be nebulized. Pulmonary administration is further described in International Publication No. WO 94/20069, which describes the pulmonary delivery of chemically modified proteins.

It is also contemplated that certain formulations can be administered orally. In one embodiment of the present invention. PLA2G12A polypeptide or PLA2G12A mutant polypeptide that are administered in this fashion can be formulated with or without those carriers customarily used in the compounding of solid dosage forms such as tablets and capsules. For example, a capsule can be designed to release the active portion of the formulation at the point in the gastrointestinal tract when bioavailability is maximized and pre-systemic degradation is minimized. Additional agents can be included to facilitate absorption of the PLA2G12A polypeptide or PLA2G12A mutant polypeptide. Diluents, flavorings, low melting point waxes, vegetable oils, lubricants, suspending agents, tablet disintegrating agents, and binders can also be employed.

Another pharmaceutical composition can involve an effective quantity of a PLA2G12A polypeptide or PLA2G12A mutant polypeptide in a mixture with non-toxic excipients that are suitable for the manufacture of tablets. By dissolving the tablets in sterile water, or another appropriate vehicle, solutions can be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional PLA2G12A polypeptide or PLA2G12A mutant polypeptide pharmaceutical compositions will be evident to those skilled in the art, including formulations involving PLA2G12A polypeptide or PLA2G12A mutant polypeptide in sustained- or controlled-delivery formulations. Techniques for formulating a variety of other sustained- or controlled-delivery means, such as liposome carriers, bio-erodible microparticles or porous beads and depot injections, are also known to those skilled in the art (see, e.g., International Publication No. WO 93/15722, which describes the controlled release of porous polymeric microparticles for the delivery of pharmaceutical compositions, and Wischke & Schwendeman, 2008, Int. J. Pharm. 364: 298-327, and Freiberg & Zhu, 2004, Int. J. Pharm. 282: 1-18, which discuss microsphere/microparticle preparation and use). As described herein, a hydrogel is an example of a sustained- or controlled-delivery formulation.

Additional examples of sustained-release preparations include semipermeable polymer matrices in the form of shaped articles, e.g. films, or microcapsules. Sustained release matrices can include polyesters, hydrogels, polylactides (U.S. Pat. No. 3,773,919 and European Patent No. 0 058 481), copolymers of L-glutamic acid and gamma ethyl-L-glutamate (Sidman et al., 1983, Biopolymers 22: 547-56), poly(2-hydroxyethyl-methacrylate) (Langer et al., 1981. J. Biomed. Mater. Res. 15: 167-277 and Langer, 1982. Chem. Tech. 12: 98-105), ethylene vinyl acetate (Langer et al., supra) or poly-D(−)-3-hydroxybutyric acid (European Patent No. 0 133 988). Sustained-release compositions can also include liposomes, which can be prepared by any of several methods known in the art. See, e.g., Epstein et al., 1985, Proc. Natl. Acad. Sci. U.S.A. 82: 3688-92; and European Patent Nos. 0 036 676, 0 088 046, and 0 143 949.

A PLA2G12A polypeptide or PLA2G12A mutant polypeptide pharmaceutical composition to be used for in vivo administration typically should be sterile. This can be accomplished by filtration through sterile filtration membranes. Where the composition is lyophilized, sterilization using this method can be conducted either prior to, or following, lyophilization and reconstitution. The composition for parenteral administration can be stored in lyophilized form or in a solution. In addition, parenteral compositions generally are placed into a container having a sterile access port, for example, an intravenous solution bag or vial having a stopper pierceable by a hypodermic injection needle.

Once the pharmaceutical composition has been formulated, it can be stored in sterile vials as a solution, suspension, gel, emulsion, solid, or as a dehydrated or lyophilized powder. Such formulations can be stored either in a ready-to-use form or in a form (e.g., lyophilized) requiring reconstitution prior to administration.

In a specific embodiment, the present invention is directed to kits for producing a single-dose administration unit. The kits can each contain both a first container having a dried protein and a second container having an aqueous formulation. Also included within the scope of this invention are kits containing single and multi-chambered pre-filled syringes (e.g., liquid syringes and lyosyringes).

The effective amount of a PLA2G12A polypeptide or PLA2G12A mutant polypeptide pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which a PLA2G12A polypeptide or PLA2G12A mutant polypeptide is being used, the route of administration, and the size (body weight, body surface, or organ size) and condition (the age and general health) of the patient. Accordingly, the clinician can titer the dosage and modify the route of administration to obtain the optimal therapeutic effect. A typical dosage can range from about 0.1 µg/kg to up to about 100 mg/kg or more, depending on the factors mentioned above. In other embodiments, the dosage can range from 0.1 µg/kg up to about 100 mg/kg; or 1 µg/kg up to about 100 mg/kg; or 5 µg/kg, 10 µg/kg, 15 µg/kg, 20 µg/kg, 25 µg/kg, 30 µg/kg, 35 µg/kg, 40 µg/kg, 45 µg/kg, 50 µg/kg, 55 µg/kg, 60 µg/kg, 65 µg/kg, 70 µg/kg, 75 µg/kg, up to about 100 mg/kg. In yet other embodiments, the dosage can be 50 µg/kg, 100 µg/kg, 150 µg/kg, 200 µg/kg, 250 µg/kg, 300 µg/kg, 350 µg/kg, 400 µg/kg, 450 µg/kg, 500 µg/kg, 550 µg/kg, 600 µg/kg, 650 µg/kg, 700 µg/kg, 750 µg/kg, 800 pig/kg, 850 µg/kg, 900 µg/kg, 950 µg/kg, 100 µg/kg, 200 µg/kg, 300 µg/kg, 400 µg/kg, 500 µg/kg, 600 µg/kg, 700 µg/kg, 800 µg/kg, 900 µg/kg, 1000 µg/kg, 2000 µg/kg, 3000 µg/kg, 4000 g/kg, 5000 µg/kg, 6000 µg/kg, 7000 µG/kg, 8000 µg/kg, 9000 µg/kg or 10 mg/kg.

The frequency of dosing will depend upon the pharmacokinetic parameters of the PLA2G12A polypeptide or PLA2G12A mutant polypeptide in the formulation being used. Typically, a clinician will administer the composition until a dosage is reached that achieves the desired effect. The composition can therefore be administered as a single dose, as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages can be ascertained through use of appropriate dose-response data.

The route of administration of the pharmaceutical composition is in accord with known methods, e.g., orally; through injection by intravenous, intraperitoneal, intracerebral (intraparenchymal), intracerebroventricular, intramuscular, intraocular, intraarterial, intraportal, or intralesional routes; by sustained release systems (which may also be injected); or by implantation devices. Where desired, the compositions can be administered by bolus injection or continuously by infusion, or by implantation device.

Alternatively or additionally, the composition can be administered locally via implantation of a membrane, sponge, or other appropriate material onto which the desired molecule has been absorbed or encapsulated. Where an implantation device is used, the device can be implanted into any suitable tissue or organ, and delivery of the desired molecule can be via diffusion, timed-release bolus, or continuous administration.

In order to deliver drug, e.g., a PLA2G12A polypeptide or PLA2G12A mutant polypeptide, at a predetermined rate such that the drug concentration can be maintained at a desired therapeutically effective level over an extended period, a variety of different approaches can be employed. In one example, a hydrogel comprising a polymer such as a gelatin (e.g., bovine gelatin, human gelatin, or gelatin from another source) or a naturally-occurring or a synthetically generated polymer can be employed. Any percentage of polymer (e.g., gelatin) can be employed in a hydrogel, such as 5, 10, 15 or 20%. The selection of an appropriate concentration can depend on a variety of factors, such as the therapeutic profile desired and the pharmacokinetic profile of the therapeutic molecule.

Examples of polymers that can be incorporated into a hydrogel include polyethylene glycol ("PEG"), polyethylene oxide, polyethylene oxide-co-polypropylene oxide, co-polyethylene oxide block or random copolymers, polyvinyl alcohol, poly(vinyl pyrrolidinone), poly(amino acids), dextran, heparin, polysaccharides, polyethers and the like.

Another factor that can be considered when generating a hydrogel formulation is the degree of crosslinking in the hydrogel and the crosslinking agent. In one embodiment, cross-linking can be achieved via a methacrylation reaction involving methacrylic anhydride. In some situations, a high degree of cross-linking may be desirable while in other situations a lower degree of crosslinking is preferred. In some cases a higher degree of crosslinking provides a longer sustained release. A higher degree of crosslinking may provide a firmer hydrogel and a longer period over which drug is delivered.

Any ratio of polymer to crosslinking agent (e.g., methacrylic anhydride) can be employed to generate a hydrogel with desired properties. For example, the ratio of polymer to crosslinker can be, e.g., 8:1, 16:1, 24:1, or 32:1. For example, when the hydrogel polymer is gelatin and the crosslinker is methacrylate, ratios of 8:1, 16:1, 24:1, or 32:1 methyacrylic anhydride:gelatin can be employed.

IV. THERAPEUTIC USES

PLA2G12A polypeptides and PLA2G12A mutant polypeptides can be used to treat, diagnose or ameliorate, a metabolic condition or disorder. In one embodiment, the metabolic disorder to be treated is diabetes, e.g., type 2 diabetes. In another embodiment, the metabolic condition or disorder is obesity. In other embodiments the metabolic condition or disorder is dyslipidemia, elevated glucose levels, elevated insulin levels or diabetic nephropathy. For example, a metabolic condition or disorder that can be treated or ameliorated using a PLA2G12A polypeptide or PLA2G12A mutant polypeptide includes a state in which a human subject has a fasting blood glucose level of 125 mg/dL or greater, for example 130, 135, 140, 145, 150, 155, 160, 165, 170, 175, 180, 185, 190, 195, 200 or greater than 200 mg/dL. Blood glucose levels can be determined in the fed or fasted state, or at random. The metabolic condition or disorder can also comprise a condition in which a subject is at increased risk of developing a metabolic condition. For a human subject, such conditions include a fasting blood glucose level of 100 mg/dL. Conditions that can be treated using a pharmaceutical composition comprising a PLA2G12A polypeptide or PLA2G12A mutant polypeptide can also be found in the American Diabetes Association Standards of Medical Care in Diabetes Care-2011, American Diabetes Association, Diabetes Care Vol. 34, No. Supplement 1, S11-S61, 2010, incorporated herein by reference.

In application, a metabolic disorder or condition, such as Type 2 diabetes, elevated glucose levels, elevated insulin levels, dyslipidemia, insulin resistance, metabolic syndrome, diabetic nephropathy or obesity, can be treated by administering a therapeutically effective dose of a PLA2G12A polypeptide, e.g., a human PLA2G12A polypeptide such as SEQ ID NOs: 1 or 3, or of a PLA2G12A mutant polypeptide, e.g., such as SEQ ID NO:9, 11, 13, 15, 17, 19, 21, 23, 25 or 27) to a patient in need thereof. The administration can be performed as described herein, such as by IV injection, intraperitoneal (IP) injection, subcutaneous injection, intramuscular injection, or orally in the form of a tablet or liquid formation. In some situations, a therapeutically effective or preferred dose of a PLA2G12A polypeptide or PLA2G12A mutant polypeptide can be determined by a clinician. A therapeutically effective dose of PLA2G12A polypeptide or PLA2G12A mutant polypeptide will depend, inter alia, upon the administration schedule, the unit dose of agent administered, whether the PLA2G12A polypeptide or PLA2G12A mutant polypeptide is administered in combination with other therapeutic agents, the immune status and the health of the recipient. The term "therapeutically effective dose," as used herein, means an amount of PLA2G12A polypeptide or PLA2G12A mutant polypeptide that elicits a biological or medicinal response in a tissue system, animal, or human being sought by a researcher, medical doctor, or other clinician, which includes alleviation or amelioration of the symptoms of the disease or disorder being treated, i.e., an amount of a PLA2G12A polypeptide or PLA2G12A mutant polypeptide that supports an observable level of one or more desired biological or medicinal response, for example lowering blood glucose, insulin, triglyceride, or cholesterol levels; reducing body weight; or improving glucose tolerance, energy expenditure, or insulin sensitivity.

It is noted that a therapeutically effective dose of a PLA2G12A polypeptide or PLA2G12A mutant polypeptide can also vary with the desired result. Thus, for example, in situations in which a lower level of blood glucose is indicated a dose of PLA2G12A polypeptide or PLA2G12A mutant polypeptide will be correspondingly higher than a dose in which a comparatively lower level of blood glucose is desired. Conversely, in situations in which a higher level of blood glucose is indicated a dose of PLA2G12A polypeptide or PLA2G12A mutant polypeptide will be correspondingly lower than a dose in which a comparatively higher level of blood glucose is desired.

In various embodiments, a subject is a human having a blood glucose level of 100 mg/dL or greater can be treated with a PLA2G12A polypeptide or PLA2G12A mutant polypeptide.

In one embodiment, a method of the instant disclosure comprises first measuring a baseline level of one or more metabolically-relevant compounds such as glucose, insulin, cholesterol, lipid in a subject. A pharmaceutical composition comprising a PLA2G12A polypeptide or PLA2G12A mutant polypeptide is then administered to the subject. After a desired period of time, the level of the one or more metabolically-relevant compounds (e.g., blood glucose, insulin, cholesterol, lipid) in the subject is again measured. The two levels can then be compared in order to determine the relative change in the metabolically-relevant compound in the subject. Depending on the outcome of that comparison another dose of the pharmaceutical composition comprising a PLA2G12A polypeptide or PLA2G12A mutant polypeptide can be administered to achieve a desired level of one or more metabolically-relevant compound.

It is noted that a pharmaceutical composition comprising a PLA2G12A polypeptide or PLA2G12A mutant polypeptide can be co-administered with another compound. The identity and properties of compound co-administered with the PLA2G12A polypeptide or PLA2G12A mutant polypeptide will depend on the nature of the condition to be treated or ameliorated. A non-limiting list of examples of compounds that can be administered in combination with a pharmaceutical composition comprising a PLA2G12A polypeptide or PLA2G12A mutant polypeptide include rosiglitizone, pioglitizone, repaglinide, nateglitinide, metformin, exenatide, stiagliptin, pramlintide, glipizide, glimeprirideacarbose, and miglitol.

V. KITS

Also provided are kits for practicing the disclosed methods. Such kits can comprise a pharmaceutical composition such as those described herein, including nucleic acids encoding the peptides or proteins provided herein, vectors and cells comprising such nucleic acids, and pharmaceutical compositions comprising such nucleic acid-containing compounds, which can be provided in a sterile container. Optionally, instructions on how to employ the provided pharmaceutical composition in the treatment of a metabolic disorder can also be included or be made available to a patient or a medical service provider.

In one aspect, a kit comprises (a) a pharmaceutical composition comprising a therapeutically effective amount of a PLA2G12A polypeptide or PLA2G12A mutant polypeptide; and (b) one or more containers for the pharmaceutical composition. For example, the kit may contain a syrine or other device to faciliatate administration of the pharmaceutical composition. In some embodiments, the syringe or other device as provided in the kit may contain the pharmaceutical composition (e.g., preloaded with one or more doses of the pharmaceutical composition). Such a kit can also comprise instructions for the use thereof; the instructions can be tailored to the precise metabolic disorder being treated. The instructions can describe the use and nature of the materials provided in the kit. In certain embodiments, kits include instructions for a patient to carry out administration to treat a metabolic disorder, such as elevated glucose levels, elevated insulin levels, obesity, type 2 diabetes, dyslipidemia or diabetic nephropathy.

Instructions can be printed on a substrate, such as paper or plastic, etc., and can be present in the kits as a package insert, in the labeling of the container of the kit or components thereof (e.g., associated with the packaging), etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, such as over the internet, are provided. An example of this embodiment is a kit that includes a web address where the instructions can be viewed and/or from which the instructions can be downloaded.

Often it will be desirable that some or all components of a kit are packaged in suitable packaging to maintain sterility. The components of a kit can be packaged in a kit containment element to make a single, easily handled unit, where the kit containment element, e.g., box or analogous structure, may or may not be an airtight container, e.g., to further preserve the sterility of some or all of the components of the kit.

EXAMPLES

The following examples, including the experiments conducted and the results achieved, are provided for illustrative purposes only and are not to be construed as limiting the present invention.

Example 1

Preparation of PLA2G12A Mutant Polypeptide

A polynucleotide encoding wild type human PLA2G12A polypeptide (SEQ ID NOs:3) is cloned from human liver cDNA library. DNA encoding the wild type human PLA2G12A polypeptide is mutagenized using Quickchange site-directed mutagenesis kit (Stratagene) well known and routinely utilized in the art.

Briefly, primer pairs containing the designed mutations are incorporated into the newly synthesized DNA molecules. The newly synthesized (mutant PLA2G12A) coding sequence is tagged with a polynucleotide encoding human Fc fragment at the C-terminus of the encoded protein. The parental template is digested with Dpn I endonuclease. The nicked vector DNA containing the desired mutant(s) is transformed into XL 1-Blue $E.$ $coli$. Plasmids encoding mutant PLA2G12A are recovered from the transformed $E.$ $coli$. The presence of the mutation(s) in the plasmids is confirmed by DNA sequencing analysis and the mutant PLA2G12A-Fc constructs are transfected into CHO cells for protein expression using DHFR-based vector set and chemically-defined media. Recombinant Fc-fused PLA2G12A mutant polypeptides are isolated from culture media of transfected CHO cells. Productions (i.e., fermentations) may involve growth of transfected CHO cells in either shaker flasks or bioreactor vessels with the mutant PLA2G12A-Fc secreted to the medium.

Purification of Fc-fused PLA2G12A mutant polypeptides is performed as follows. Cultures are typically harvested after 4-6 days of protein production and crude supernatant is isolated from cells via centrifugation or hollow fiber filtration for shaker flask and bioreactor productions, respectively. The crude mixture is then either loaded directly or concentrated 10×-20× and buffer-exchanged into 20 mM sodium phosphate, pH 7.2, 300 mM NaCl, 0.05% azide and loaded onto mAbSelect Sure resin (GE Biosciences). The resin is then washed with the same high salt phosphate buffer 5-10 times and the bound protein is eluted with 300 mM citrate, pH 3.4. Eluted fractions are neutralized with 1 M Tris buffer, pH 8.0. In order to enrich the Protein A affinity purified material to greater than 90% full-length protein, high-resolution Hydrophobic Interaction Chromatography (HIC) chromatography is utilized. A pH-neutralized pool is loaded directly onto a pre-packed Biosuite Phenyl HIC column (Waters) resulting in the bulk of the clipped species flowing through, and the bulk of the full-length protein adhering to the column. Mutant PLA2G12A-Fc proteins are eluted via a linear gradient to 100% Milli-Q $H_2O$. Fractions are analyzed for percentage of the full-length protein via N-terminal sequence (NTS) and were pooled accordingly. An HIC pool is then concentrated and further purified via preparative size-exclusion chromatography (SEC) with PBS, pH 7.2, 10% glycerol, 50 μM EDTA as the mobile phase. The non-aggregated SEC product is concentrated to 5 mg/mL if necessary, aliquoted and flash frozen.

Example 2

PLA2G12A Expression in Mouse Model

The effect of AAV-mediated PLAG12A expression on the phenotype of mice fed a high fat diet (D12492i, Research Diet, New Brunswick, N.J.) was investigated. Mice in which PLA2G12A polypeptide was over expressed were observed, inter alia, to maintain body weight despite comparable food intake, have improved glucose tolerance, improved insulin tolerance and lower blood glucose compared to mice who received an empty vector.

Study Design.

Age-matched young adults (5 week old) male B6D2F1 mice (Jackson Labs) were fed a 60% high-fat diet to elicit diet-induced obesity (DIO). After six weeks on the diet, the mice were randomized into two groups (n=10-12/group) based on body weight as well as fasting blood levels of glucose and insulin. AAV viral particles were packaged and titered prior to injection as follows: (i) AAV8-PLA2G12A and (ii) AAV-empty vector (control). The animals were kept on the high-fat diet until termination of the study. The mice were monitored for changes in body weight, food intake, lean muscle mass and fat mass over a 15 week period post injection.

Body Weight.

Body weight was followed throughout the study, both before and after injection. As shown in FIG. 1, the body weight of the groups was comparable before injection. The body weight of the animals receiving an injection of AAV8-empty vector (control animals) increased markedly over the course of the study whereas the body weight of the animals receiving injection of AAV8-PLA2G12A (the AAV8-PLA2G12A group of animals) remained relatively constant. The difference in body weight between the control animals and PLA2G12A animals reached statistical significance at all time points after injection.

Food Intake.

Figure 2:
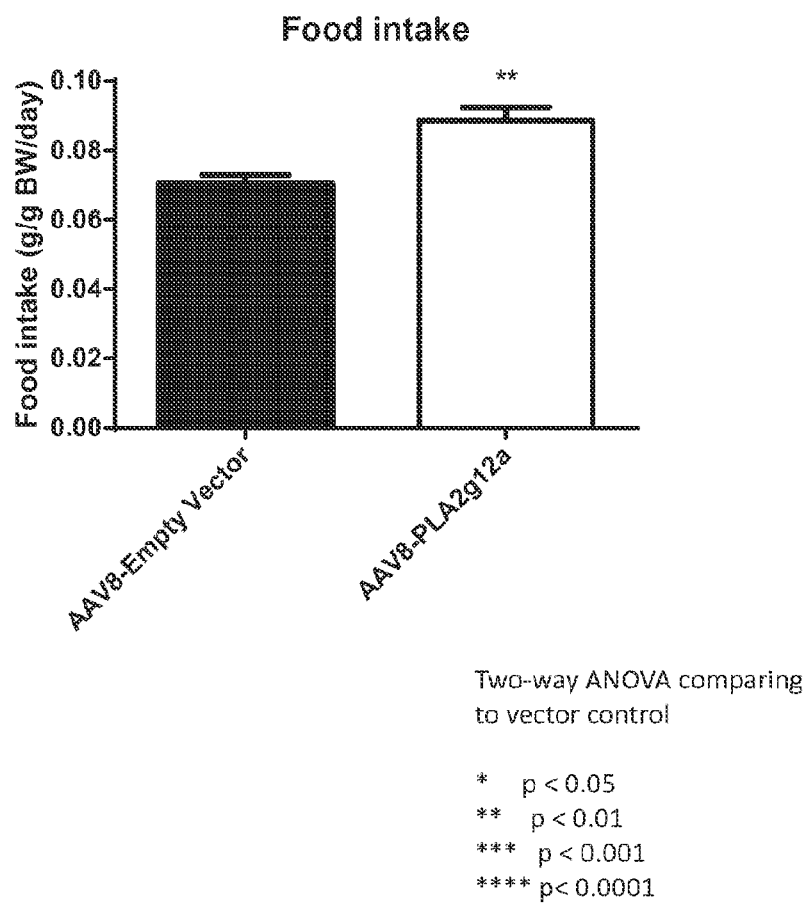
FIG. 2 is a bar graph showing average food intake (gig BW/day) of AAV8-PLA2G12A mice and AAV8-empty vector (control) mice during a 7-day period between week 11 and 12 after AAV injection.

Food intake was also followed during the study. Average daily food intake was determined by weighing the remaining uneaten food in the mouse cage during a 7-day period between week 11 and 12 after AAV injection. As shown in FIG. 2, food intake of the AAV8-PLA2G12A group of animals was greater than the food intake of the control animals. Thus, the lower body weight observed in the PLA2G12A animals was not due to decreased food intake. Rather, the AAV8-PLA2G12A group of animals were able to maintain their lower body weight while consuming a larger amount of food than the control animals.

Glucose.

Figure 3:
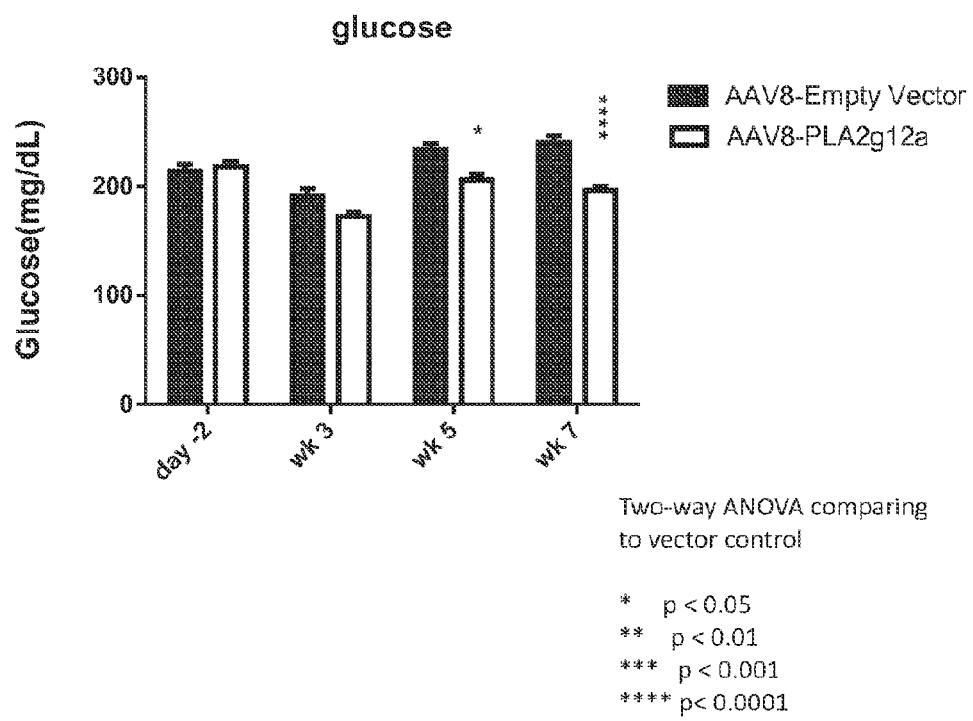
FIG. 3 is a bar graph showing the level of blood glucose in AAV8-PLA2G12A mice and AAV8-empty vector (control) mice measured two days before injection and at weeks 3, 5 and 7 after injection.

Glucose levels were measured in blood samples collected from 4 hr fasted animals two days before injection and at weeks 3, 5 and 7 after injection. As shown in FIG. 3, the glucose levels of groups were comparable before injection (with the glucose level of the AAV8-PLA2G12A animals slightly higher than that of the AAV8-empty vector (control) animals). At 3, 5 and 7 weeks post injection, the glucose level of the AAV8-PLA2G12A animals had markedly decreased relative to the glucose level of the AAV8-empty vector (control) animals, reaching statistical significance at weeks 5 and 7.

Glucose Tolerance.

Figure 4:
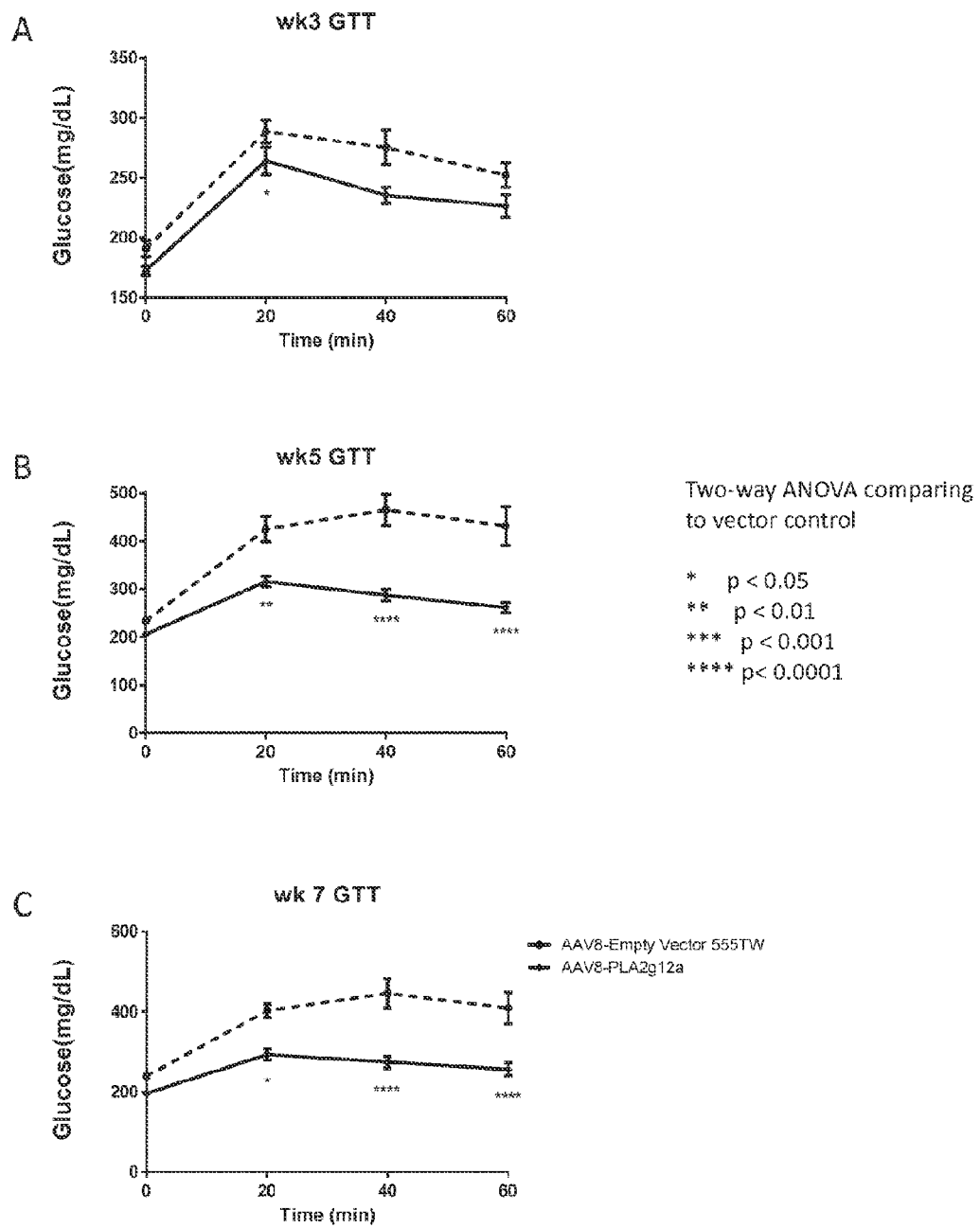
FIG. 4 is a series of three plots showing the results of glucose tolerance tests performed at week 3 (FIG. 4A), week 5 (FIG. 4B) and week 7 (FIG. 4C) after injection. Each plot shows glucose levels (mg/dL) over a 60 minute period after p.o. injection of glucose (2 g/kg) in AAV8-PLA2G12A mice and AAV8-empty vector (control) mice.

Three oral glucose tolerance tests (OGTT), in animals fasted for 4 hr, were performed during the study. At 3 weeks post injection, the glucose tolerance of the AAV8-PLA2G12A group of animals was somewhat better than that observed in control animals, as demonstrated by glucose levels and glucose AUC over the 60 minute period after p.o. administration of glucose (2 g/kg). See FIG. 4A.

At 5 and 7 weeks post injection, the glucose tolerance of the AAV8-PLA2G12A group of animals was considerably better than that observed in control animals, as demonstrated by glucose levels and glucose AUC over the 60 minute period after p.o. administration of glucose (2 g/kg). The difference in glucose level for the AAV8-PLA2G12A group of animals and the control animals reached statistical significance at the 20, 40 and 60 minute measurements. See FIGS. 4B and C.

Insulin Tolerance.

Figure 5:
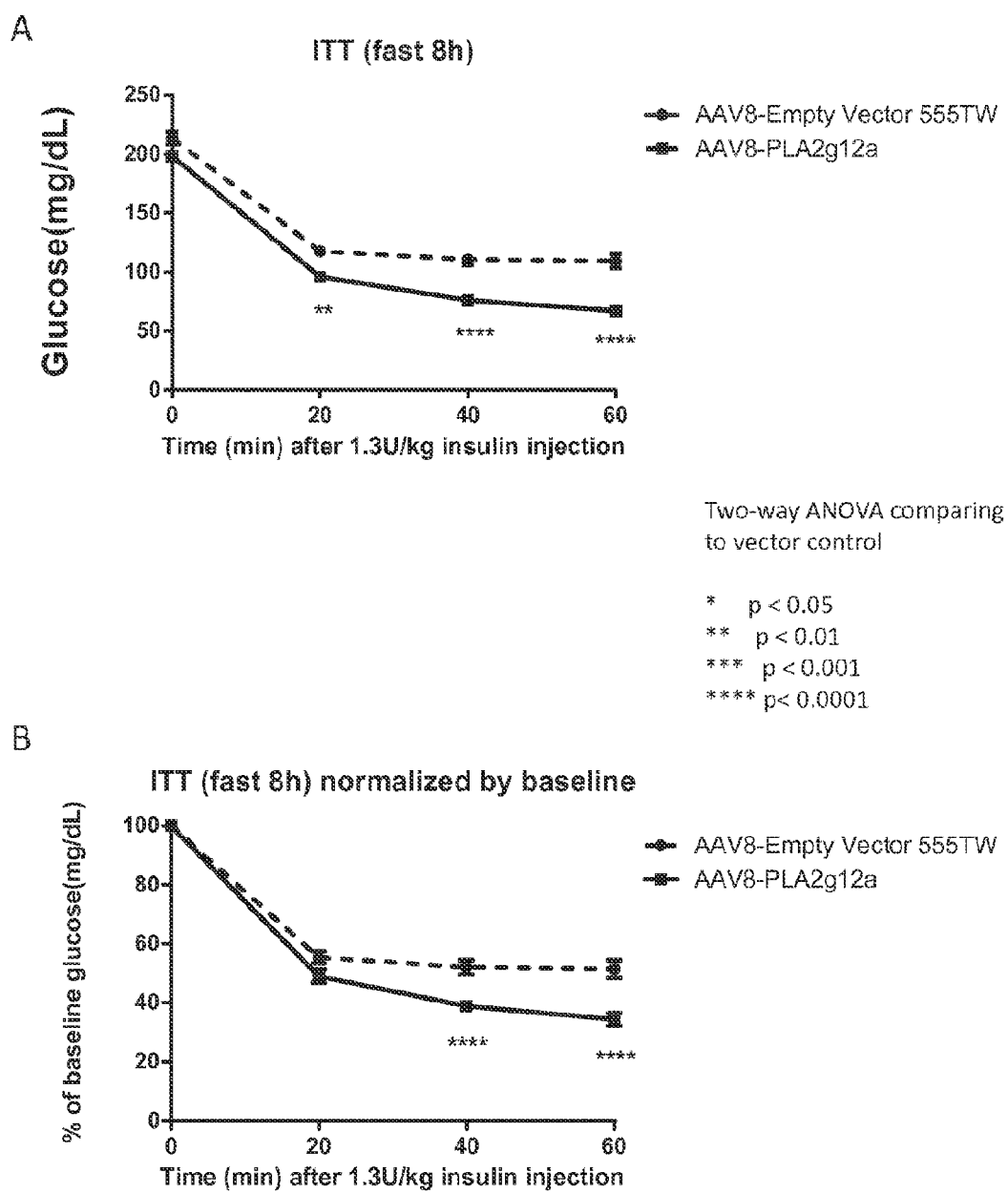
FIG. 5 is a series of two plots showing the results of an insulin sensitivity test performed 9 weeks after injection. Glucose levels over a 60 minute period after i.p. injection of 1 U/kg insulin in AAV8-PLA2G12A mice and AAV8-empty vector (control) mice are shown in FIG. 5A (as mg/dL) and in FIG. 5B (as % of baseline).

An insulin tolerance test was conducted 9 weeks after injection, in animals fasted for 4 hr. As shown in FIG. 5A, the insulin tolerance in the AAV8-PLA2G12A group of animals was better than that observed in the control animals, as demonstrated by glucose levels and glucose AUC over the 60 minute period after i.p. injection of insulin (1.3 U/kg). The difference in glucose level for the AAV8-PLA2G12A group of animals and the control animals reached statistical significance at the 20, 40 and 60 minute measurements. FIG. 5B shows the glucose level plotted in terms of % baseline.

Insulin.

Figure 6:
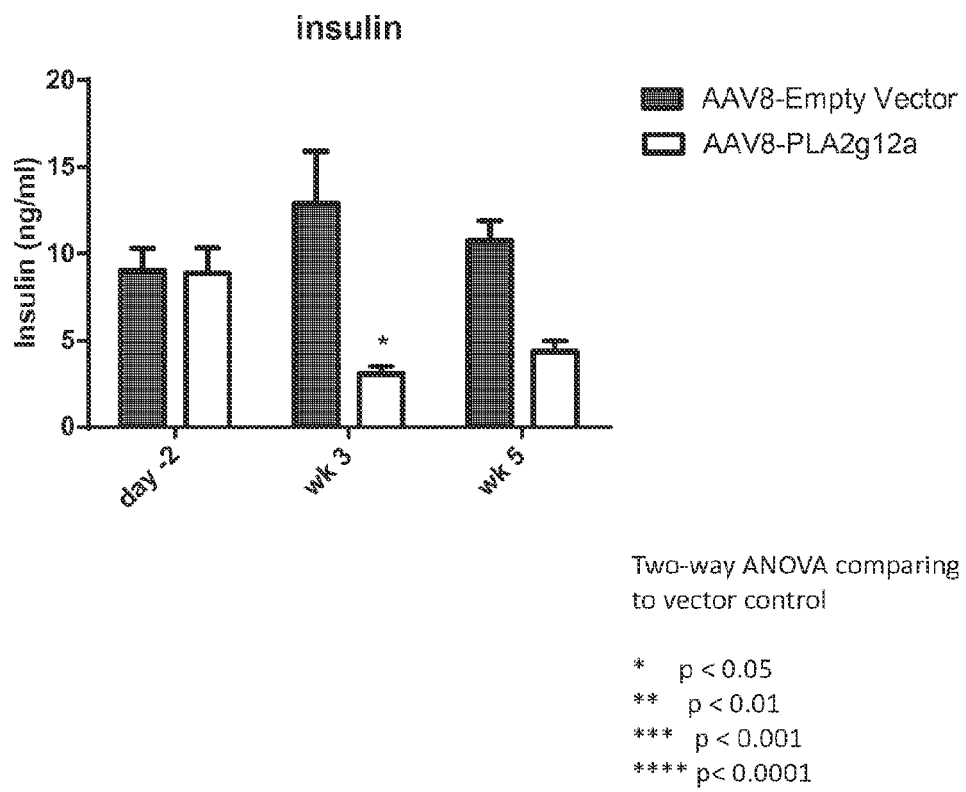
FIG. 6 is a bar graph showing the level of serum insulin in AAV8-PLA2G12A mice and AAV8-empty vector (control) mice measured two days before injection and at weeks 3 and 5 after injection.

Insulin levels were measured in blood samples collected from 4 hr fasted animals two days before injection and at weeks 3 and 5 after injection. As shown in FIG. 6, the insulin levels of PLA2G12A and control animals were comparable before injection. At 3 and 5 weeks post injection, the insulin levels of the AAV8-PLA2G12A group of animals was markedly decreased while the insulin levels of the control animals was markedly increased. The difference in insulin levels in the AAV8-PLA2G12A group of animals and control animals reached statistical significance at week 3.

Triglyceride and Cholesterol.

Figure 7:
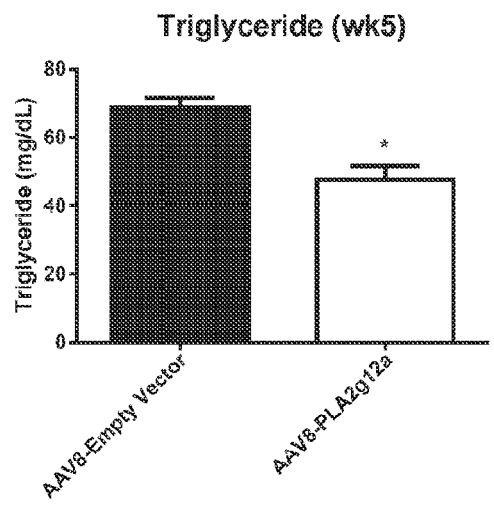
FIG. 7 is a series of two bar graphs showing levels of serum triglyceride (FIG. 7A) and serum cholesterol (FIG. 7B) in AAV8-PLA2G12A mice and AAV8-empty vector (control) mice measured at week 5 after injection.
Figure 7:
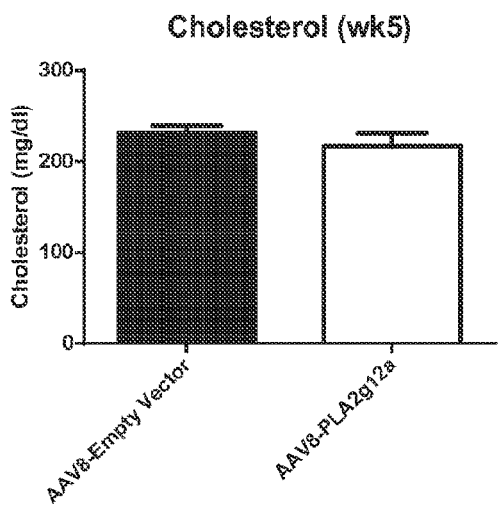

Triglyceride and total cholesterol levels were measured in blood samples collected from 4 hr fasted animals at week 5. As shown in FIG. 7A, the triglyceride level in the AAV8-PLA2G12A group of animals was significantly lower than the level in the control animals. As shown in FIG. 7B, the cholesterol level in the PLA2G12A animals was somewhat lower than the levels in the control animals, but the difference did not reach statistical significance.

Fat and Lean Mass.

Figure 8:
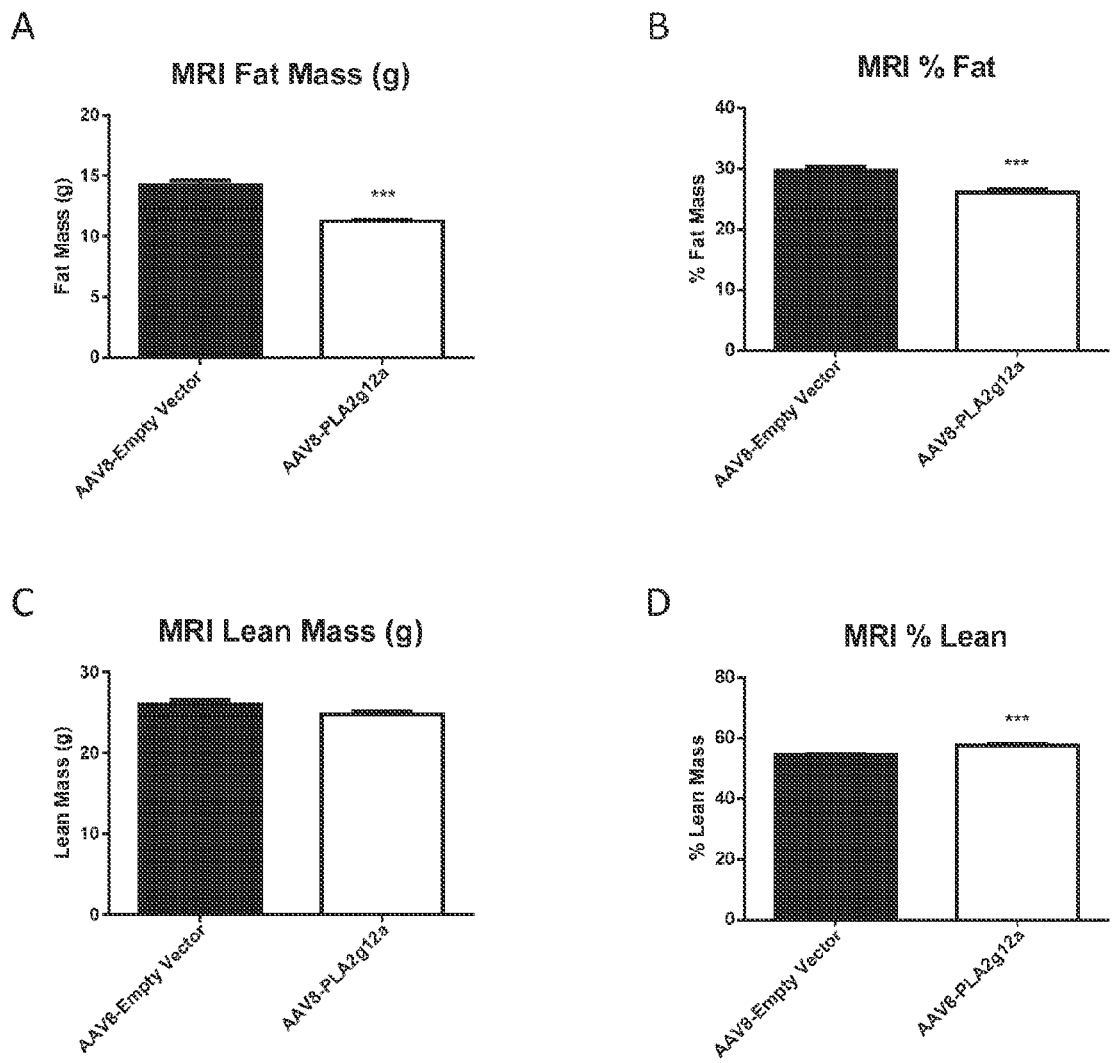
FIG. 8 is a series of four bar graphs showing fat mass and lean mass of AAV8-PLA2G12A mice and AAV8-empty vector (control) mice measured 8 weeks after injection. Fat mass of the animals is shown in FIGS. 8A(g) and 8B (% fat). Lean mass of the animals is shown in FIGS. 8C (g) and 8D (% lean).

Eight weeks after injection, the fat and lean mass of PLA2G12A and control mice were measured using non-destructive and non-invasive whole body composition analysis (minispec, Bruker Corporation, Billerica, Mass.). As shown in FIG. 8A, the AAV8-PLA2G12A group of animals had significantly lower fat mass (g) than the control animals. Likewise, as shown in FIG. 8B, in terms of percent fat, the fat mass of the PLA2G12A animals was significantly lower than the control animals.

As shown in FIG. 8C, the lean mass (g) of the AAV8-PLA2G12A group of animals was lower than that of the control animals, but the difference did not reach statistical significance. As shown in FIG. 8D, in terms of percent fat, the fat mass of the PLA2G12A animals was significantly lower than the control animals.

Conclusions

The over-expression of PLA2G12A in mice resulted in, inter alia, maintenance of body weight (despite increased food intake), improved glucose tolerance, improved insulin tolerance and lower blood glucose compared to controls. The data shows that PLA2G12A expression improves the metabolic profile and that PLA2G12A can be leveraged for treatment or amelioration of a metabolic disorder, such as type 2 diabetes, elevated glucose levels, elevated insulin levels, obesity or diabetic nephropathy, including by administering a therapeutic amount of PLA2G12A polypeptide to a subject in need thereof.//

Example 3

PLA2G12A-H110L Expression in Mouse Model

The effect of AAV-mediated PLAG12A-H110L expression on the phenotype of mice fed a high fat diet (D12492i, Research Diet, New Brunswick, N.J.) also was examined. Mice in which the PLA2G12A mutant polypeptide, PLA2G12A-H110L, was over expressed were observed, inter alia, to have decreased body weight, lower blood glucose, and improved glucose tolerance compared to mice receiving an empty vector, and surprisingly to mice receiving AAVS-PLAG12A.

Study Design.

Age-matched young adults (5 week old) male B6D2F1 mice (Jackson Labs, Bar Harbor, Me.) were fed a 60% high-fat diet to elicit diet-induced obesity (DIO). After six weeks on the diet, the mice were randomized into three groups (n=10/group) based on body weight as well as fasting blood levels of glucose and insulin. AAV viral particles were packaged and titered prior to injection as follows: (i) AAV8-PLA2G12A, (ii) AAV8-PLA2G12A-H110L, and (iii) AAV-empty vector (control). The animals were kept on the high-fat diet until termination of the study. The animals also were monitored for changes in body weight.

Body Weight.

Figure 9:
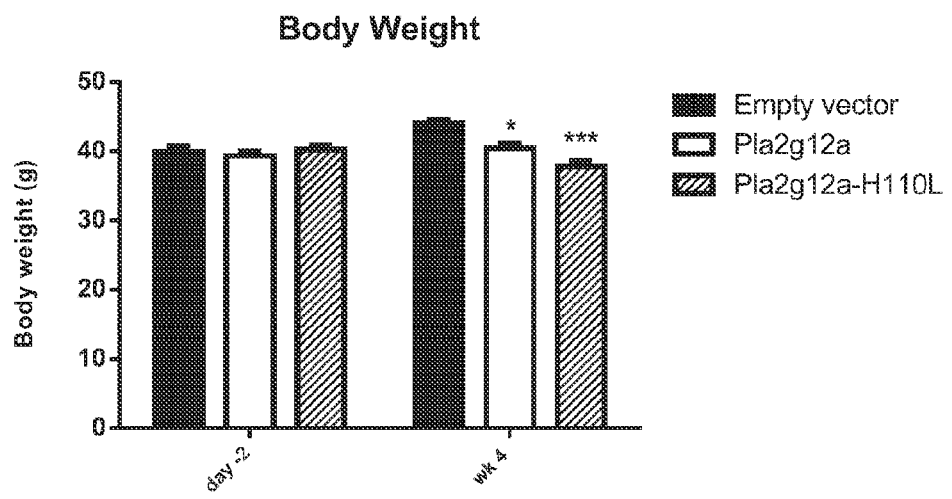
FIG. 9 is a bar graph showing body weight (g) of AAV8-PLA2G12A mice, AAV8-PLA2G12A-H110L mice and AAV8-empty vector (control) mice. The body weight was measured two days before injection and at week 4 after injection.

Body weight was followed throughout the study, both before and after injection. As shown in FIG. 9, the body weight of the groups was comparable before injection. At 4 weeks post injection, the body weight of the animals receiving an injection of AAV8-empty vector (control) animals had increased. The body weight of the animals receiving injection of AAV8-PLA2G12A remained relatively constant, but was significantly lower than that of the control animals. The body weight of the animals receiving injection of AAV8-PLA2G12A-H110L was decreased and was significantly lower than that of the control animals. In addition, the body weight of the PLA2G12A animals was decreased even with respect to the PLA2G12A animals, demonstrating superiority of the PLA2G12A mutant polypeptide, PLA2G12A-H110L, over the wild-type PLA2G12A polypeptide in lowering body weight.

Glucose.

Figure 10:
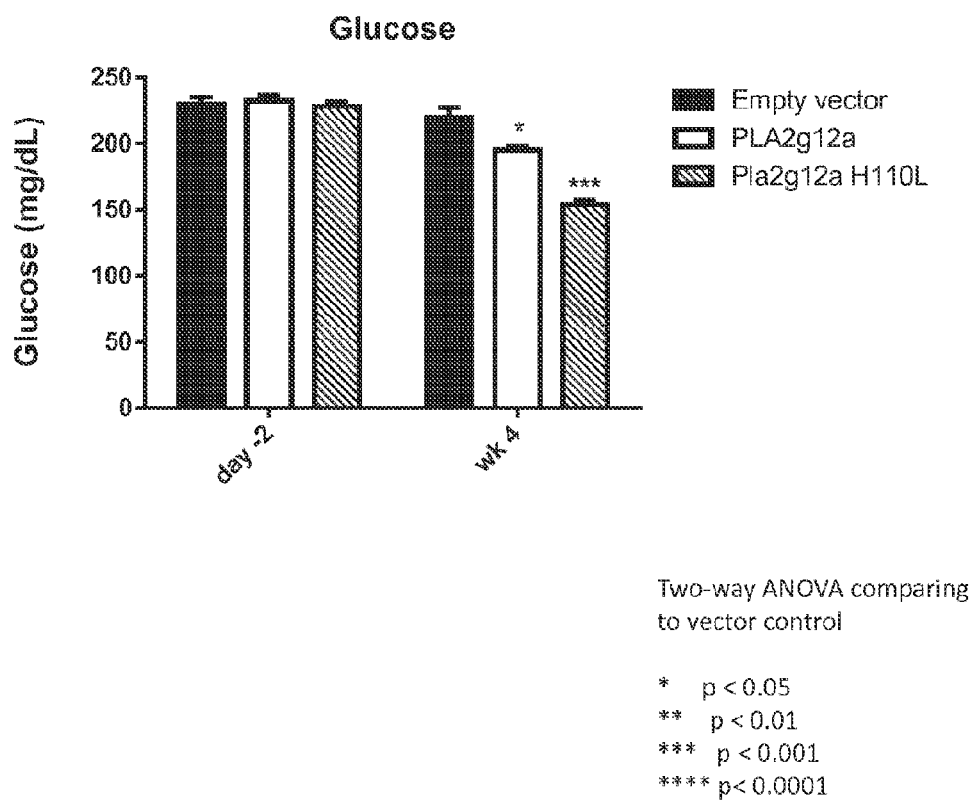
FIG. 10 is a bar graph showing the level of blood glucose in AAV8-PLA2G12A mice, AAV8-PLA2G12A-H110L mice and AAV8-empty vector (control) mice measured two days before injection and at week 4 after injection.

Glucose levels were measured in blood samples collected from 4 hr fasted animals two days before injection and at week 4 after injection. As shown in FIG. 10, the glucose levels of groups were comparable before injection. At 4 weeks post injection, glucose levels of the AAV8-PLA2G12A animals were significantly decreased compared to control animals. In addition, the glucose level of the AAV8-PLA2G12A-H110L animals was decreased even with respect to the AAV8-PLA2G12A animals, demonstrating superiority of the PLA2G12A mutant polypeptide, PLA2G12A-H110L, over the wild-type PLA2G12A polypeptide in lowering glucose levels.

Glucose Tolerance.

Figure 11:
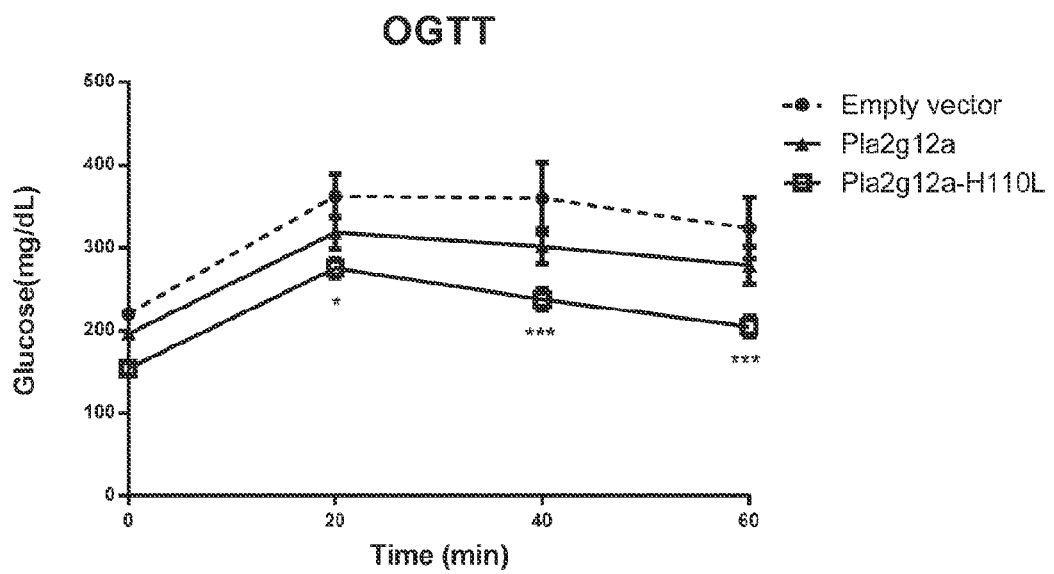
FIG. 11 is a plot showing the results of a glucose tolerance test performed at week 4 after injection. The plot shows glucose levels (mg/dL) over a 60 minute period after p.o. injection of glucose (2 g/kg) in AAV8-PLA2G12A mice, AAV8-PLA2G12A-H110L mice, and AAV8-empty vector (control) mice.

Three oral glucose tolerance tests (OGTT), in animals faster for 4 hr, were performed during the study. At 4 weeks post injection, the glucose tolerance of the AAV8-PLA2G12A group of animals was better than that observed in control animals, as demonstrated by glucose levels and glucose AUC over the 60 minute period after p.o. administration of glucose (2 g/kg), but did not reach statistical significance. The glucose tolerance of the AAV8-PLA2G12A-H110L animals was better than that observed in control animals, reaching statistical significance at the 20, 40 and 60 minute measurements. In addition, the glucose tolerance of the AAV8-PLA2G12A-H110L animals also was better than that observed in the AAV8-PLA2G12A animals, demonstrating superiority of the PLA2G12A mutant polypeptide, PLA2G12A-H110L, over the wild-type PLA2G12A polypeptide in improving glucose tolerance. See FIG. 11.

Insulin.

Figure 12:
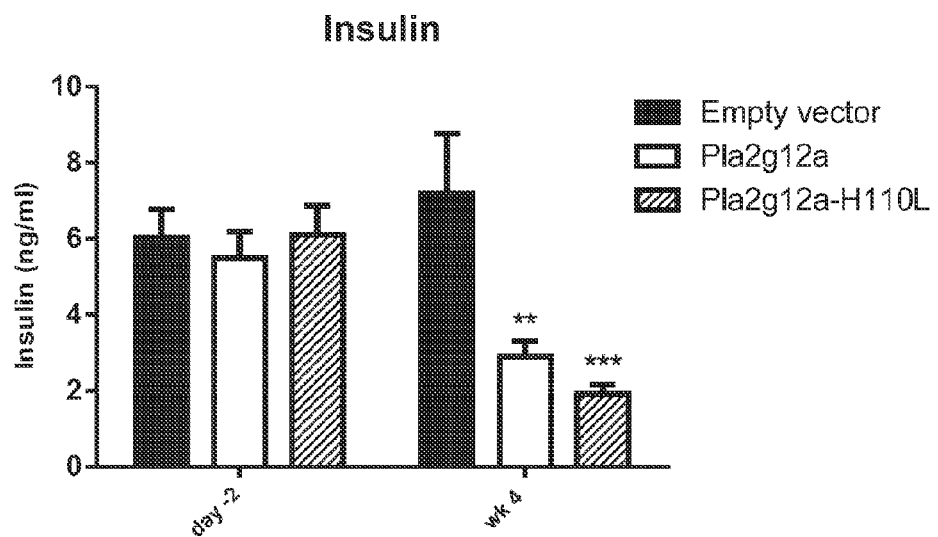
FIG. 12 is a bar graph showing the level of serum insulin (ng/ml) in AAV8-PLA2G12A mice, AAV8-PLA2G12A-H110L mice and AAV8-empty vector (control) mice measured two days before injection and at week 4 after injection.

Insulin levels were measured in blood samples collected from 4 hr fasted animals two days before injection and at week 4 after injection. As shown in FIG. 12, the insulin levels of AAV8-PLA2G12A-H110L, AAV8-PLA2G12A, and AAV8-empty vector (control) animals were comparable before injection (with the insulin level of the AAV8-PL2G12A animals slightly lower than the AAV8-empty vector animals and the AAV8-PLA2G12A-H110L animals). At 4 weeks post injection, the insulin levels of the control animals were increased. The insulin levels of the AAV8-PLA2G12A animals were significantly decreased compared to control animals. The insulin levels of the AAV8-PLA2G12A-H110L animals were significantly decreased with respect to the controls. In addition, the insulin levels of the AAV8-PLA2G12A-H110L animals were even decreased with respect to the AAV8-PLA2G12A animals, demonstrating superiority of the PLA2G12A mutant polypeptide, PLA2G12A-H110L, over the wild-type PLA2G12A polypeptide in lowering insulin levels.

Conclusions

The expression of the PLA2G12A mutant polypeptide, PLA2G12A-H110L, in mice resulted, inter alia, in decreased body weight, lowered blood glucose, lowered serum insulin, and improved glucose tolerance compared to control animals receiving AAV8-empty vector, as well as compared to animals receiving AAV8-PLA2G12A. The data shows that expression of the PLA2G12A mutant polypeptide, PLA2G12A-H110L, improves the metabolic profile, surprisingly, even over that of PLA2G12A polypeptide. Accordingly, PLA2G12A mutant polypeptide, PLA2G12A-H110L, can be leveraged for treatment or amelioration of a metabolic disorder, such as type 2 diabetes, elevated glucose levels, elevated insulin levels, obesity or diabetic nephropathy, including by administering a therapeutic amount of the PLA2G12A mutant polypeptide, PLA2G12A-H110L, to a subject in need thereof.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of treating a metabolic disorder comprising administering to a subject in need thereof a therapeutically effective amount of an isolated human PLA2G12A mutant polypeptide comprising an amino acid sequence that has at least 90% sequence identity with SEQ ID NO: 1 and comprises an amino acid substitution at position 110.

2. The method of claim 1, wherein the metabolic disorder is type 2 diabetes.

3. The method of claim 1, wherein the metabolic disorder is dyslipidemia.

4. The method of claim 1, wherein the metabolic disorder is obesity.

5. The method of claim 1, wherein the metabolic disorder comprises a condition in which the subject has a fasting blood glucose level of greater than or equal to 100 mg/dL.

6. The method of claim 1, wherein the subject is a mammal.

7. The method of claim 6, wherein the mammal is a human.

8. The method of claim 1, wherein the PLA2G12A mutant polypeptide is administered in the form of a pharmaceutical composition comprising the PLA2G12A mutant polypeptide in admixture with a pharmaceutically-acceptable carrier.

9. The method of claim 1, further comprising the step of determining the subject's blood glucose level at a timepoint subsequent to the administration.

10. The method of claim 1, further comprising the step of determining the subject's serum insulin level at a timepoint subsequent to the administration.

11. The method of claim 1, wherein the PLA2G12A mutant polypeptide comprises an amino acid sequence that has at least 90% sequence identity with SEQ ID NO: 9, 13, 17, 21, or 25.

12. The method of claim 11, wherein the PLA2G12A mutant polypeptide comprises the amino acid sequence of SEQ ID NO: 9, 13, 17, 21, or 25.

13. A method of treating a metabolic disorder comprising administering to a subject in need thereof a therapeutically effective amount of an isolated PLA2G12A mutant polypeptide comprising an amino acid sequence that has at least 90% sequence identity with SEQ ID NO: 3, and comprises an amino acid substitution at position 88.

14. The method of claim 13, wherein the metabolic disorder is type 2 diabetes.

15. The method of claim 13, wherein the metabolic disorder is dyslipidemia.

16. The method of claim 13, wherein the metabolic disorder is obesity.

17. The method of claim 13, wherein the metabolic disorder comprises a condition in which the subject has a fasting blood glucose level of greater than or equal to 100 mg/dL.

18. The method of claim 13, wherein the subject is a mammal.

19. The method of claim 18, wherein the mammal is a human.

20. The method of claim 13, wherein the PLA2G12A mutant polypeptide is administered in the form of a pharmaceutical composition comprising the PLA2G12A mutant polypeptide in admixture with a pharmaceutically-acceptable carrier.

21. The method of claim 13, further comprising the step of determining the subject's blood glucose level at a time-point subsequent to the administration.

22. The method of claim 13, further comprising the step of determining the subject's serum insulin level at a time-point subsequent to the administration.

23. The method of claim 13, wherein the PLA2G12A mutant polypeptide comprises an amino acid sequence that has at least 90% sequence identity with SEQ ID NO: 11, 15, 19, 23, or 27.

24. The method of claim 23, wherein the PLA2G12A mutant polypeptide comprises the amino acid sequence of SEQ ID NO: 11, 15, 19, 23 or 27.

* * * * *

SEQUENCE LISTING

```
<160> NUMBER OF SEQ ID NOS: 28

<210> SEQ ID NO 1
<211> LENGTH: 189
<212> TYPE: PRT
<213> ORGANISM: Homo sapiens

<400> SEQUENCE: 1

Met Ala Leu Leu Ser Arg Pro Ala Leu Thr Leu Leu Leu Leu Leu Met
1               5                   10                  15

Ala Ala Val Val Arg Cys Gln Glu Gln Ala Gln Thr Thr Asp Trp Arg
            20                  25                  30

Ala Thr Leu Lys Thr Ile Arg Asn Gly Val His Lys Ile Asp Thr Tyr
        35                  40                  45

Leu Asn Ala Ala Leu Asp Leu Leu Gly Gly Glu Asp Gly Leu Cys Gln
    50                  55                  60

Tyr Lys Cys Ser Asp Gly Ser Lys Pro Phe Pro Arg Tyr Gly Tyr Lys
65                  70                  75                  80

Pro Ser Pro Pro Asn Gly Cys Gly Ser Pro Leu Phe Gly Val His Leu
                85                  90                  95

Asn Ile Gly Ile Pro Ser Leu Thr Lys Cys Cys Asn Gln His Asp Arg
            100                 105                 110

Cys Tyr Glu Thr Cys Gly Lys Ser Lys Asn Asp Cys Asp Glu Glu Phe
        115                 120                 125

Gln Tyr Cys Leu Ser Lys Ile Cys Arg Asp Val Gln Lys Thr Leu Gly
    130                 135                 140

Leu Thr Gln His Val Gln Ala Cys Glu Thr Thr Val Glu Leu Leu Phe
145                 150                 155                 160

Asp Ser Val Ile His Leu Gly Cys Lys Pro Tyr Leu Asp Ser Gln Arg
                165                 170                 175

Ala Ala Cys Arg Cys His Tyr Glu Glu Lys Thr Asp Leu
            180                 185

<210> SEQ ID NO 2
```

<211> LENGTH: 570
<212> TYPE: DNA
<213> ORGANISM: Homo sapiens

<400> SEQUENCE: 2

```
atggccctgc tctcgcgccc cgcgctcacc ctcctgctcc tcctcatggc cgctgttgtc      60
aggtgccagg agcaggccca gaccaccgac tggagagcca ccctgaagac catccggaac     120
ggcgttcata agatagacac gtacctgaac gccgccttgg acctcctggg aggcgaggac     180
ggtctctgcc agtataaatg cagtgacgga tctaagcctt tcccacgtta tggttataaa     240
ccctccccac cgaatggatg tggctctcca ctgtttggtg ttcatcttaa cattggtatc     300
ccttccctga caaagtgttg caaccaacac gacaggtgct atgagacctg tggcaaaagc     360
aagaatgact gtgatgaaga attccagtat gcctctcca agatctgccg agatgtacag     420
aaaacactag gactaactca gcatgttcag gcatgtgaaa caacagtgga gctcttgttt     480
gacagtgtta tacatttagg ttgtaaacca tatctggaca gccaacgagc cgcatgcagg     540
tgtcattatg aagaaaaaac tgatctttaa                                      570
```

<210> SEQ ID NO 3
<211> LENGTH: 167
<212> TYPE: PRT
<213> ORGANISM: Homo sapiens

<400> SEQUENCE: 3

```
Gln Glu Gln Ala Gln Thr Thr Asp Trp Arg Ala Thr Leu Lys Thr Ile
1               5                   10                  15
Arg Asn Gly Val His Lys Ile Asp Thr Tyr Leu Asn Ala Ala Leu Asp
            20                  25                  30
Leu Leu Gly Gly Glu Asp Gly Leu Cys Gln Tyr Lys Cys Ser Asp Gly
        35                  40                  45
Ser Lys Pro Phe Pro Arg Tyr Gly Tyr Lys Pro Ser Pro Pro Asn Gly
    50                  55                  60
Cys Gly Ser Pro Leu Phe Gly Val His Leu Asn Ile Gly Ile Pro Ser
65                  70                  75                  80
Leu Thr Lys Cys Cys Asn Gln His Asp Arg Cys Tyr Glu Thr Cys Gly
                85                  90                  95
Lys Ser Lys Asn Asp Cys Asp Glu Glu Phe Gln Tyr Cys Leu Ser Lys
            100                 105                 110
Ile Cys Arg Asp Val Gln Lys Thr Leu Gly Leu Thr Gln His Val Gln
        115                 120                 125
Ala Cys Glu Thr Thr Val Glu Leu Leu Phe Asp Ser Val Ile His Leu
    130                 135                 140
Gly Cys Lys Pro Tyr Leu Asp Ser Gln Arg Ala Ala Cys Arg Cys His
145                 150                 155                 160
Tyr Glu Glu Lys Thr Asp Leu
                165
```

<210> SEQ ID NO 4
<211> LENGTH: 504
<212> TYPE: DNA
<213> ORGANISM: Homo sapiens

<400> SEQUENCE: 4

```
caggagcagg cccagaccac cgactggaga gccaccctga agaccatccg gaacggcgtt      60
cataagatag acacgtacct gaacgccgcc ttggacctcc tgggaggcga ggacggtctc     120
```

| | |
|---|---|
| tgccagtata aatgcagtga cggatctaag cctttcccac gttatggtta taaaccctcc | 180 |
| ccaccgaatg gatgtggctc tccactgttt ggtgttcatc ttaacattgg tatcccttcc | 240 |
| ctgacaaagt gttgcaacca acacgacagg tgctatgaga cctgtggcaa aagcaagaat | 300 |
| gactgtgatg aagaattcca gtattgcctc tccaagatct gccgagatgt acagaaaaca | 360 |
| ctaggactaa ctcagcatgt tcaggcatgt gaaacaacag tggagctctt gtttgacagt | 420 |
| gttatacatt taggttgtaa accatatctg gacagccaac gagccgcatg caggtgtcat | 480 |
| tatgaagaaa aaactgatct ttaa | 504 |

<210> SEQ ID NO 5
<211> LENGTH: 192
<212> TYPE: PRT
<213> ORGANISM: Mus musculus

<400> SEQUENCE: 5

Met Val Thr Pro Arg Pro Ala Pro Ala Arg Ser Pro Ala Leu Leu Leu
1               5                   10                  15

Leu Leu Leu Leu Ala Thr Ala Arg Gly Gln Glu Gln Asp Gln Thr Thr
            20                  25                  30

Asp Trp Arg Ala Thr Leu Lys Thr Ile Arg Asn Gly Ile His Lys Ile
        35                  40                  45

Asp Thr Tyr Leu Asn Ala Ala Leu Asp Leu Leu Gly Gly Glu Asp Gly
    50                  55                  60

Leu Cys Gln Tyr Lys Cys Ser Asp Gly Ser Lys Pro Val Pro Arg Tyr
65                  70                  75                  80

Gly Tyr Lys Pro Ser Pro Pro Asn Gly Cys Gly Ser Pro Leu Phe Gly
                85                  90                  95

Val His Leu Asn Ile Gly Ile Pro Ser Leu Thr Lys Cys Cys Asn Gln
            100                 105                 110

His Asp Arg Cys Tyr Glu Thr Cys Gly Lys Ser Lys Asn Asp Cys Asp
        115                 120                 125

Glu Glu Phe Gln Tyr Cys Leu Ser Lys Ile Cys Arg Asp Val Gln Lys
    130                 135                 140

Thr Leu Gly Leu Ser Gln Asn Val Gln Ala Cys Glu Thr Thr Val Glu
145                 150                 155                 160

Leu Leu Phe Asp Ser Val Ile His Leu Gly Cys Lys Pro Tyr Leu Asp
                165                 170                 175

Ser Gln Arg Ala Ala Cys Trp Cys Arg Tyr Glu Glu Lys Thr Asp Leu
            180                 185                 190

<210> SEQ ID NO 6
<211> LENGTH: 579
<212> TYPE: DNA
<213> ORGANISM: Mus musculus

<400> SEQUENCE: 6

| | |
|---|---|
| atggtgactc cgcggcccgc gcccgcccgg agcccgcgc tcctcctcct cctgctgctg | 60 |
| gccactgcgc gtgggcagga acaggaccag accaccgact ggagggccac cctcaagacc | 120 |
| atccgcaacg gcatccacaa gatagacacg tacctcaacg ccgcgctgga cctgctgggc | 180 |
| ggggaggacg ggctctgcca gtacaagtgc agcgacggat cgaagcctgt tccacgctat | 240 |
| ggatataaac catctccacc aaatggctgt ggctcgccac tgtttggcgt tcatctgaac | 300 |
| ataggtatcc cttccctgac caagtgctgc aaccagcacg acagatgcta cgagacctgc | 360 |
| gggaaaagca agaacgactg tgacgaggag ttccagtact gcctctccaa gatctgcaga | 420 |

```
gacgtgcaga agacgctcgg actatctcag aacgtccagg catgtgagac aacggtggag    480
ctcctctttg acagcgtcat ccatttaggc tgcaagccat acctggacag ccagcgggct    540
gcatgctggt gtcgttatga agaaaaaaca gatctataa                            579
```

```
<210> SEQ ID NO 7
<211> LENGTH: 167
<212> TYPE: PRT
<213> ORGANISM: Mus musculus

<400> SEQUENCE: 7
```

```
Gln Glu Gln Asp Gln Thr Thr Asp Trp Arg Ala Thr Leu Lys Thr Ile
  1               5                  10                  15

Arg Asn Gly Ile His Lys Ile Asp Thr Tyr Leu Asn Ala Ala Leu Asp
             20                  25                  30

Leu Leu Gly Gly Glu Asp Gly Leu Cys Gln Tyr Lys Cys Ser Asp Gly
         35                  40                  45

Ser Lys Pro Val Pro Arg Tyr Gly Tyr Lys Pro Ser Pro Pro Asn Gly
     50                  55                  60

Cys Gly Ser Pro Leu Phe Gly Val His Leu Asn Ile Gly Ile Pro Ser
 65                  70                  75                  80

Leu Thr Lys Cys Cys Asn Gln His Asp Arg Cys Tyr Glu Thr Cys Gly
                 85                  90                  95

Lys Ser Lys Asn Asp Cys Asp Glu Glu Phe Gln Tyr Cys Leu Ser Lys
            100                 105                 110

Ile Cys Arg Asp Val Gln Lys Thr Leu Gly Leu Ser Gln Asn Val Gln
        115                 120                 125

Ala Cys Glu Thr Thr Val Glu Leu Leu Phe Asp Ser Val Ile His Leu
    130                 135                 140

Gly Cys Lys Pro Tyr Leu Asp Ser Gln Arg Ala Ala Cys Trp Cys Arg
145                 150                 155                 160

Tyr Glu Glu Lys Thr Asp Leu
                165
```

```
<210> SEQ ID NO 8
<211> LENGTH: 504
<212> TYPE: DNA
<213> ORGANISM: Mus musculus

<400> SEQUENCE: 8
```

```
caggaacagg accagaccac cgactggagg gccaccctca agaccatccg caacggcatc     60
cacaagatag acacgtacct caacgccgcg ctggacctgc tgggcgggga ggacgggctc    120
tgccagtaca agtgcagcga cggatcgaag cctgttccac gctatggata taaaccatct    180
ccaccaaatg gctgtggctc gccactgttt ggcgttcatc tgaacatagg tatcccttcc    240
ctgaccaagt gctgcaacca gcacgacaga tgctacgaga cctgcgggaa aagcaagaac    300
gactgtgacg aggagttcca gtactgcctc tccaagatct gcagagacgt gcagaagacg    360
ctcggactat ctcagaacgt ccaggcatgt gagacaacgg tggagctcct ctttgacagc    420
gtcatccatt taggctgcaa gccatacctg gacagccagc gggctgcatg ctggtgtcgt    480
tatgaagaaa aaacagatct ataa                                           504
```

```
<210> SEQ ID NO 9
<211> LENGTH: 189
<212> TYPE: PRT
<213> ORGANISM: Homo sapiens
```

<400> SEQUENCE: 9

Met Ala Leu Leu Ser Arg Pro Ala Leu Thr Leu Leu Leu Leu Met
1               5                   10                  15

Ala Ala Val Val Arg Cys Gln Glu Gln Ala Gln Thr Thr Asp Trp Arg
            20                  25                  30

Ala Thr Leu Lys Thr Ile Arg Asn Gly Val His Lys Ile Asp Thr Tyr
        35                  40                  45

Leu Asn Ala Ala Leu Asp Leu Gly Gly Glu Asp Gly Leu Cys Gln
    50                  55                  60

Tyr Lys Cys Ser Asp Gly Ser Lys Pro Phe Pro Arg Tyr Gly Tyr Lys
65                  70                  75                  80

Pro Ser Pro Pro Asn Gly Cys Gly Ser Pro Leu Phe Gly Val His Leu
                85                  90                  95

Asn Ile Gly Ile Pro Ser Leu Thr Lys Cys Cys Asn Gln Leu Asp Arg
                100                 105                 110

Cys Tyr Glu Thr Cys Gly Lys Ser Lys Asn Asp Cys Asp Glu Phe
            115                 120                 125

Gln Tyr Cys Leu Ser Lys Ile Cys Arg Asp Val Gln Lys Thr Leu Gly
    130                 135                 140

Leu Thr Gln His Val Gln Ala Cys Glu Thr Thr Val Glu Leu Leu Phe
145                 150                 155                 160

Asp Ser Val Ile His Leu Gly Cys Lys Pro Tyr Leu Asp Ser Gln Arg
                165                 170                 175

Ala Ala Cys Arg Cys His Tyr Glu Glu Lys Thr Asp Leu
            180                 185

<210> SEQ ID NO 10
<211> LENGTH: 570
<212> TYPE: DNA
<213> ORGANISM: Homo sapiens

<400> SEQUENCE: 10
atggccctgc tctcgcgccc cgcgctcacc ctcctgctcc tcctcatggc cgctgttgtc     60
aggtgccagg agcaggccca gaccaccgac tggagagcca ccctgaagac catccggaac    120
ggcgttcata agatagacac gtacctgaac gccgccttgg acctcctggg aggcgaggac    180
ggtctctgcc agtataaatg cagtgacgga tctaagcctt tcccacgtta tggttataaa    240
ccctccccac cgaatggatg tggctctcca ctgtttggtg ttcatcttaa cattggtatc    300
ccttccctga caaagtgttg caaccaactc gacaggtgct atgagacctg tggcaaaagc    360
aagaatgact gtgatgaaga attccagtat tgcctctcca agatctgccg agatgtacag    420
aaaacactag gactaactca gcatgttcag gcatgtgaaa caacagtgga gctcttgttt    480
gacagtgtta tacatttagg ttgtaaacca tatctggaca gccaacgagc cgcatgcagg    540
tgtcattatg aagaaaaaac tgatctttaa                                      570

<210> SEQ ID NO 11
<211> LENGTH: 167
<212> TYPE: PRT
<213> ORGANISM: Homo sapiens

<400> SEQUENCE: 11

Gln Glu Gln Ala Gln Thr Thr Asp Trp Arg Ala Thr Leu Lys Thr Ile
1               5                   10                  15

Arg Asn Gly Val His Lys Ile Asp Thr Tyr Leu Asn Ala Ala Leu Asp

```
                  20                  25                  30

Leu Leu Gly Gly Glu Asp Gly Leu Cys Gln Tyr Lys Cys Ser Asp Gly
            35                  40                  45

Ser Lys Pro Phe Pro Arg Tyr Gly Tyr Lys Pro Ser Pro Asn Gly
    50                  55                  60

Cys Gly Ser Pro Leu Phe Gly Val His Leu Asn Ile Gly Ile Pro Ser
65                  70                  75                  80

Leu Thr Lys Cys Cys Asn Gln Leu Asp Arg Cys Tyr Glu Thr Cys Gly
                85                  90                  95

Lys Ser Lys Asn Asp Cys Asp Glu Glu Phe Gln Tyr Cys Leu Ser Lys
            100                 105                 110

Ile Cys Arg Asp Val Gln Lys Thr Leu Gly Leu Thr Gln His Val Gln
            115                 120                 125

Ala Cys Glu Thr Thr Val Glu Leu Leu Phe Asp Ser Val Ile His Leu
        130                 135                 140

Gly Cys Lys Pro Tyr Leu Asp Ser Gln Arg Ala Ala Cys Arg Cys His
145                 150                 155                 160

Tyr Glu Glu Lys Thr Asp Leu
            165
```

<210> SEQ ID NO 12
<211> LENGTH: 504
<212> TYPE: DNA
<213> ORGANISM: Homo sapiens

<400> SEQUENCE: 12

```
caggagcagg cccagaccac cgactggaga gccaccctga agaccatccg gaacggcgtt      60
cataagatag acacgtacct gaacgccgcc ttggacctcc tgggaggcga ggacggtctc     120
tgccagtata atgcagtga cggatctaag ccttttccac gttatggtta taaccctcc      180 ccaccgaatg gatgtggctc tccactgttt ggtgttcatc ttaacattgg tatcccttcc     240
ctgacaaagt gttgcaacca actcgacagg tgctatgaga cctgtggcaa aagcaagaat     300
gactgtgatg aagaattcca gtattgcctc tccaagatct gccgagatgt acagaaaaca     360
ctaggactaa ctcagcatgt tcaggcatgt gaaacaacag tggagctctt gtttgacagt     420
gttatacatt taggttgtaa accatatctg gacagccaac gagccgcatg caggtgtcat     480
tatgaagaaa aaactgatct ttaa                                            504
```

<210> SEQ ID NO 13
<211> LENGTH: 189
<212> TYPE: PRT
<213> ORGANISM: Homo sapiens

<400> SEQUENCE: 13

```
Met Ala Leu Leu Ser Arg Pro Ala Leu Thr Leu Leu Leu Leu Leu Met
1               5                  10                  15

Ala Ala Val Val Arg Cys Gln Glu Gln Ala Gln Thr Thr Asp Trp Arg
            20                  25                  30

Ala Thr Leu Lys Thr Ile Arg Asn Gly Val His Lys Ile Asp Thr Tyr
        35                  40                  45

Leu Asn Ala Ala Leu Asp Leu Leu Gly Gly Glu Asp Gly Leu Cys Gln
    50                  55                  60

Tyr Lys Cys Ser Asp Gly Ser Lys Pro Phe Pro Arg Tyr Gly Tyr Lys
65                  70                  75                  80

Pro Ser Pro Pro Asn Gly Cys Gly Ser Pro Leu Phe Gly Val His Leu
```

-continued

```
                      85                  90                  95
Asn Ile Gly Ile Pro Ser Leu Thr Lys Cys Cys Asn Gln Met Asp Arg
                100                 105                 110
Cys Tyr Glu Thr Cys Gly Lys Ser Lys Asn Asp Cys Asp Glu Glu Phe
            115                 120                 125
Gln Tyr Cys Leu Ser Lys Ile Cys Arg Asp Val Gln Lys Thr Leu Gly
        130                 135                 140
Leu Thr Gln His Val Gln Ala Cys Glu Thr Thr Val Glu Leu Leu Phe
145                 150                 155                 160
Asp Ser Val Ile His Leu Gly Cys Lys Pro Tyr Leu Asp Ser Gln Arg
                165                 170                 175
Ala Ala Cys Arg Cys His Tyr Glu Glu Lys Thr Asp Leu
                180                 185

<210> SEQ ID NO 14
<211> LENGTH: 570
<212> TYPE: DNA
<213> ORGANISM: Homo sapiens

<400> SEQUENCE: 14
atggccctgc tctcgcgccc cgcgctcacc ctcctgctcc tcctcatggc cgctgttgtc      60
aggtgccagg agcaggccca gaccaccgac tggagagcca ccctgaagac catccggaac     120
ggcgttcata gatagacac gtacctgaac gccgccttgg acctcctggg aggcgaggac     180
ggtctctgcc agtataaatg cagtgacgga tctaagcctt tcccacgtta tggttataaa     240
ccctccccac cgaatggatg tggctctcca ctgtttggtg ttcatcttaa cattggtatc     300
ccttccctga caaagtgttg caaccaaatg acaggtgct atgagacctg tggcaaaagc     360
aagaatgact gtgatgaaga attccagtat tgcctctcca agatctgccg agatgtacag     420
aaaacactag gactaactca gcatgttcag gcatgtgaaa caacagtgga gctcttgttt     480
gacagtgtta tacatttagg ttgtaaacca tatctggaca gccaacgagc cgcatgcagg     540
tgtcattatg aagaaaaaac tgatctttaa                                      570

<210> SEQ ID NO 15
<211> LENGTH: 167
<212> TYPE: PRT
<213> ORGANISM: Homo sapiens

<400> SEQUENCE: 15

Gln Glu Gln Ala Gln Thr Thr Asp Trp Arg Ala Thr Leu Lys Thr Ile
1               5                   10                  15
Arg Asn Gly Val His Lys Ile Asp Thr Tyr Leu Asn Ala Ala Leu Asp
            20                  25                  30
Leu Leu Gly Gly Glu Asp Gly Leu Cys Gln Tyr Lys Cys Ser Asp Gly
        35                  40                  45
Ser Lys Pro Phe Pro Arg Tyr Gly Tyr Lys Pro Ser Pro Asn Gly
    50                  55                  60
Cys Gly Ser Pro Leu Phe Gly Val His Leu Asn Ile Gly Ile Pro Ser
65                  70                  75                  80
Leu Thr Lys Cys Cys Asn Gln Met Asp Arg Cys Tyr Glu Thr Cys Gly
                85                  90                  95
Lys Ser Lys Asn Asp Cys Asp Glu Glu Phe Gln Tyr Cys Leu Ser Lys
            100                 105                 110
Ile Cys Arg Asp Val Gln Lys Thr Leu Gly Leu Thr Gln His Val Gln
        115                 120                 125
```

```
Ala Cys Glu Thr Thr Val Glu Leu Leu Phe Asp Ser Val Ile His Leu
    130                 135                 140

Gly Cys Lys Pro Tyr Leu Asp Ser Gln Arg Ala Ala Cys Arg Cys His
145                 150                 155                 160

Tyr Glu Glu Lys Thr Asp Leu
                165

<210> SEQ ID NO 16
<211> LENGTH: 504
<212> TYPE: DNA
<213> ORGANISM: Homo sapiens

<400> SEQUENCE: 16
caggagcagg cccagaccac cgactggaga gccaccctga agaccatccg gaacggcgtt      60
cataagatag acacgtacct gaacgccgcc ttggacctcc tgggaggcga ggacggtctc     120
tgccagtata atgcagtga cggatctaag cctttcccac gttatggtta taaaccctcc     180
ccaccgaatg gatgtggctc tccactgttt ggtgttcatc ttaacattgg tatcccttcc     240
ctgacaaagt gttgcaacca aatggacagg tgctatgaga cctgtggcaa aagcaagaat     300
gactgtgatg aagaattcca gtattgcctc tccaagatct gccgagatgt acagaaaaca     360
ctaggactaa ctcagcatgt tcaggcatgt gaaacaacag tggagctctt gtttgacagt     420
gttatacatt taggttgtaa accatatctg gacagccaac gagccgcatg caggtgtcat     480
tatgaagaaa aaactgatct ttaa                                            504

<210> SEQ ID NO 17
<211> LENGTH: 189
<212> TYPE: PRT
<213> ORGANISM: Homo sapiens

<400> SEQUENCE: 17

Met Ala Leu Leu Ser Arg Pro Ala Leu Thr Leu Leu Leu Leu Met
1               5                   10                  15

Ala Ala Val Val Arg Cys Gln Glu Gln Ala Gln Thr Thr Asp Trp Arg
                20                  25                  30

Ala Thr Leu Lys Thr Ile Arg Asn Gly Val His Lys Ile Asp Thr Tyr
            35                  40                  45

Leu Asn Ala Ala Leu Asp Leu Leu Gly Gly Glu Asp Gly Leu Cys Gln
        50                  55                  60

Tyr Lys Cys Ser Asp Gly Ser Lys Pro Phe Pro Arg Tyr Gly Tyr Lys
65                  70                  75                  80

Pro Ser Pro Pro Asn Gly Cys Gly Ser Pro Leu Phe Gly Val His Leu
                85                  90                  95

Asn Ile Gly Ile Pro Ser Leu Thr Lys Cys Cys Asn Gln Ala Asp Arg
                100                 105                 110

Cys Tyr Glu Thr Cys Gly Lys Ser Lys Asn Asp Cys Asp Glu Glu Phe
            115                 120                 125

Gln Tyr Cys Leu Ser Lys Ile Cys Arg Asp Val Gln Lys Thr Leu Gly
        130                 135                 140

Leu Thr Gln His Val Gln Ala Cys Glu Thr Thr Val Glu Leu Leu Phe
145                 150                 155                 160

Asp Ser Val Ile His Leu Gly Cys Lys Pro Tyr Leu Asp Ser Gln Arg
                165                 170                 175

Ala Ala Cys Arg Cys His Tyr Glu Glu Lys Thr Asp Leu
                180                 185
```

<210> SEQ ID NO 18
<211> LENGTH: 570
<212> TYPE: DNA
<213> ORGANISM: Homo sapiens

<400> SEQUENCE: 18

```
atggccctgc tctcgcgccc cgcgctcacc ctcctgctcc tcctcatggc cgctgttgtc      60
aggtgccagg agcaggccca gaccaccgac tggagagcca ccctgaagac catccggaac     120
ggcgttcata agatagacac gtacctgaac gccgccttgg acctcctggg aggcgaggac     180
ggtctctgcc agtataaatg cagtgacgga tctaagcctt tcccacgtta tggttataaa     240
ccctccccac cgaatggatg tggctctcca ctgtttggtg ttcatcttaa cattggtatc     300
ccttccctga caaagtgttg caaccaagcc gacaggtgct atgagacctg tggcaaaagc     360
aagaatgact gtgatgaaga attccagtat tgcctctcca agatctgccg agatgtacag     420
aaaacactag gactaactca gcatgttcag gcatgtgaaa caacagtgga gctcttgttt     480
gacagtgtta tacatttagg ttgtaaacca tatctggaca gccaacgagc cgcatgcagg     540
tgtcattatg aagaaaaaac tgatctttaa                                     570
```

<210> SEQ ID NO 19
<211> LENGTH: 167
<212> TYPE: PRT
<213> ORGANISM: Homo sapiens

<400> SEQUENCE: 19

```
Gln Glu Gln Ala Gln Thr Thr Asp Trp Arg Ala Thr Leu Lys Thr Ile
  1               5                  10                  15

Arg Asn Gly Val His Lys Ile Asp Thr Tyr Leu Asn Ala Ala Leu Asp
             20                  25                  30

Leu Leu Gly Gly Glu Asp Gly Leu Cys Gln Tyr Lys Cys Ser Asp Gly
         35                  40                  45

Ser Lys Pro Phe Pro Arg Tyr Gly Tyr Lys Pro Ser Pro Pro Asn Gly
 50                  55                  60

Cys Gly Ser Pro Leu Phe Gly Val His Leu Asn Ile Gly Ile Pro Ser
 65                  70                  75                  80

Leu Thr Lys Cys Cys Asn Gln Ala Asp Arg Cys Tyr Glu Thr Cys Gly
                 85                  90                  95

Lys Ser Lys Asn Asp Cys Asp Glu Glu Phe Gln Tyr Cys Leu Ser Lys
            100                 105                 110

Ile Cys Arg Asp Val Gln Lys Thr Leu Gly Leu Thr Gln His Val Gln
        115                 120                 125

Ala Cys Glu Thr Thr Val Glu Leu Leu Phe Asp Ser Val Ile His Leu
    130                 135                 140

Gly Cys Lys Pro Tyr Leu Asp Ser Gln Arg Ala Ala Cys Arg Cys His
145                 150                 155                 160

Tyr Glu Glu Lys Thr Asp Leu
                165
```

<210> SEQ ID NO 20
<211> LENGTH: 504
<212> TYPE: DNA
<213> ORGANISM: Homo sapiens

<400> SEQUENCE: 20

```
caggagcagg cccagaccac cgactggaga gccaccctga agaccatccg gaacggcgtt      60
```

```
cataagatag acacgtacct gaacgccgcc ttggacctcc tgggaggcga ggacggtctc    120
tgccagtata aatgcagtga cggatctaag cctttcccac gttatggtta taaaccctcc    180
ccaccgaatg gatgtggctc tccactgttt ggtgttcatc ttaacattgg tatcccttcc    240
ctgacaaagt gttgcaacca agccgacagg tgctatgaga cctgtggcaa aagcaagaat    300
gactgtgatg aagaattcca gtattgcctc tccaagatct gccgagatgt acagaaaaca    360
ctaggactaa ctcagcatgt tcaggcatgt gaaacaacag tggagctctt gtttgacagt    420
gttatacatt taggttgtaa accatatctg gacagccaac gagccgcatg caggtgtcat    480
tatgaagaaa aaactgatct ttaa                                          504
```

<210> SEQ ID NO 21
<211> LENGTH: 189
<212> TYPE: PRT
<213> ORGANISM: Homo sapiens

<400> SEQUENCE: 21

```
Met Ala Leu Leu Ser Arg Pro Ala Leu Thr Leu Leu Leu Leu Leu Met
1               5                   10                  15
Ala Ala Val Val Arg Cys Gln Glu Gln Ala Gln Thr Thr Asp Trp Arg
            20                  25                  30
Ala Thr Leu Lys Thr Ile Arg Asn Gly Val His Lys Ile Asp Thr Tyr
        35                  40                  45
Leu Asn Ala Ala Leu Asp Leu Leu Gly Gly Glu Asp Gly Leu Cys Gln
    50                  55                  60
Tyr Lys Cys Ser Asp Gly Ser Lys Pro Phe Pro Arg Tyr Gly Tyr Lys
65                  70                  75                  80
Pro Ser Pro Pro Asn Gly Cys Gly Ser Pro Leu Phe Gly Val His Leu
                85                  90                  95
Asn Ile Gly Ile Pro Ser Leu Thr Lys Cys Cys Asn Gln Val Asp Arg
            100                 105                 110
Cys Tyr Glu Thr Cys Gly Lys Ser Lys Asn Asp Cys Asp Glu Glu Phe
        115                 120                 125
Gln Tyr Cys Leu Ser Lys Ile Cys Arg Asp Val Gln Lys Thr Leu Gly
    130                 135                 140
Leu Thr Gln His Val Gln Ala Cys Glu Thr Thr Val Glu Leu Leu Phe
145                 150                 155                 160
Asp Ser Val Ile His Leu Gly Cys Lys Pro Tyr Leu Asp Ser Gln Arg
                165                 170                 175
Ala Ala Cys Arg Cys His Tyr Glu Glu Lys Thr Asp Leu
            180                 185
```

<210> SEQ ID NO 22
<211> LENGTH: 570
<212> TYPE: DNA
<213> ORGANISM: Homo sapiens

<400> SEQUENCE: 22

```
atggccctgc tctcgcgccc cgcgctcacc ctcctgctcc tcctcatggc cgctgttgtc     60
aggtgccagg agcaggccca gaccaccgac tggagagcca cctgaagac catccggaac    120 ggcgttcata agatagacac gtacctgaac gccgccttgg acctctggg aggcgaggac    180 ggtctctgcc agtataaatg cagtgacgga tctaagcctt tcccacgtta tggttataaa    240
ccctccccac cgaatggatg tggctctcca ctgtttggtg ttcatcttaa cattggtatc    300
```

```
ccttccctga caaagtgttg caaccaagtt gacaggtgct atgagacctg tggcaaaagc    360
aagaatgact gtgatgaaga attccagtat tgcctctcca agatctgccg agatgtacag    420
aaaacactag gactaactca gcatgttcag gcatgtgaaa caacagtgga gctcttgttt    480
gacagtgtta tacatttagg ttgtaaacca tatctggaca gccaacgagc cgcatgcagg    540
tgtcattatg aagaaaaaac tgatctttaa                                     570

<210> SEQ ID NO 23
<211> LENGTH: 167
<212> TYPE: PRT
<213> ORGANISM: Homo sapiens

<400> SEQUENCE: 23

Gln Glu Gln Ala Gln Thr Thr Asp Trp Arg Ala Thr Leu Lys Thr Ile
 1               5                  10                  15

Arg Asn Gly Val His Lys Ile Asp Thr Tyr Leu Asn Ala Ala Leu Asp
                20                  25                  30

Leu Leu Gly Gly Glu Asp Gly Leu Cys Gln Tyr Lys Cys Ser Asp Gly
            35                  40                  45

Ser Lys Pro Phe Pro Arg Tyr Gly Tyr Lys Pro Ser Pro Pro Asn Gly
        50                  55                  60

Cys Gly Ser Pro Leu Phe Gly Val His Leu Asn Ile Gly Ile Pro Ser
 65                  70                  75                  80

Leu Thr Lys Cys Cys Asn Gln Val Asp Arg Cys Tyr Glu Thr Cys Gly
                85                  90                  95

Lys Ser Lys Asn Asp Cys Asp Glu Glu Phe Gln Tyr Cys Leu Ser Lys
               100                 105                 110

Ile Cys Arg Asp Val Gln Lys Thr Leu Gly Leu Thr Gln His Val Gln
           115                 120                 125

Ala Cys Glu Thr Thr Val Glu Leu Leu Phe Asp Ser Val Ile His Leu
       130                 135                 140

Gly Cys Lys Pro Tyr Leu Asp Ser Gln Arg Ala Ala Cys Arg Cys His
145                 150                 155                 160

Tyr Glu Glu Lys Thr Asp Leu
                165

<210> SEQ ID NO 24
<211> LENGTH: 504
<212> TYPE: DNA
<213> ORGANISM: Homo sapiens

<400> SEQUENCE: 24
caggagcagg cccagaccac cgactggaga gccaccctga agaccatccg gaacggcgtt    60
cataagatag acacgtacct gaacgccgcc ttggacctcc tgggaggcga ggacggtctc   120
tgccagtata atgcagtga cggatctaag cctttcccac gttatggtta taaaccctcc    180
ccaccgaatg gatgtggctc tccactgttt ggtgttcatc ttaacattgg tatcccttcc   240
ctgacaaagt gttgcaacca agttgacagg tgctatgaga cctgtggcaa agcaagaat   300 gactgtgatg aagaattcca gtattgcctc tccaagatct gccgagatgt acagaaaaca   360
ctaggactaa ctcagcatgt tcaggcatgt gaaacaacag tggagctctt gtttgacagt   420
gttatacatt taggttgtaa accatatctg gacagccaac gagccgcatg caggtgtcat   480
tatgaagaaa aaactgatct ttaa                                           504

<210> SEQ ID NO 25
```

<211> LENGTH: 189
<212> TYPE: PRT
<213> ORGANISM: Homo sapiens

<400> SEQUENCE: 25

```
Met Ala Leu Leu Ser Arg Pro Ala Leu Thr Leu Leu Leu Leu Met
1               5                   10                  15

Ala Ala Val Val Arg Cys Gln Glu Gln Ala Gln Thr Thr Asp Trp Arg
            20                  25                  30

Ala Thr Leu Lys Thr Ile Arg Asn Gly Val His Lys Ile Asp Thr Tyr
        35                  40                  45

Leu Asn Ala Ala Leu Asp Leu Leu Gly Gly Glu Asp Gly Leu Cys Gln
    50                  55                  60

Tyr Lys Cys Ser Asp Gly Ser Lys Pro Phe Pro Arg Tyr Gly Tyr Lys
65                  70                  75                  80

Pro Ser Pro Pro Asn Gly Cys Gly Ser Pro Leu Phe Gly Val His Leu
                85                  90                  95

Asn Ile Gly Ile Pro Ser Leu Thr Lys Cys Cys Asn Gln Ile Asp Arg
            100                 105                 110

Cys Tyr Glu Thr Cys Gly Lys Ser Lys Asn Asp Cys Asp Glu Glu Phe
        115                 120                 125

Gln Tyr Cys Leu Ser Lys Ile Cys Arg Asp Val Gln Lys Thr Leu Gly
    130                 135                 140

Leu Thr Gln His Val Gln Ala Cys Glu Thr Thr Val Glu Leu Leu Phe
145                 150                 155                 160

Asp Ser Val Ile His Leu Gly Cys Lys Pro Tyr Leu Asp Ser Gln Arg
                165                 170                 175

Ala Ala Cys Arg Cys His Tyr Glu Glu Lys Thr Asp Leu
            180                 185
```

<210> SEQ ID NO 26
<211> LENGTH: 570
<212> TYPE: DNA
<213> ORGANISM: Homo sapiens

<400> SEQUENCE: 26

```
atggccctgc tctcgcgccc cgcgctcacc ctcctgctcc tcctcatggc cgctgttgtc    60
aggtgccagg agcaggccca gaccaccgac tggagagcca ccctgaagac catccggaac   120
ggcgttcata agatagacac gtacctgaac gccgccttgg acctcctggg aggcgaggac   180
ggtctctgcc agtataaatg cagtgacgga tctaagcctt tcccacgtta tggttataaa   240
ccctccccac cgaatggatg tggctctcca ctgtttggtg ttcatcttaa cattggtatc   300
ccttccctga caaagtgttg caaccaaatc gacaggtgct atgagacctg tggcaaaagc   360
aagaatgact gtgatgaaga attccagtat tgcctctcca agatctgccg agatgtacag   420
aaaacactag gactaactca gcatgttcag gcatgtgaaa caacagtgga gctcttgttt   480
gacagtgtta tacatttagg ttgtaaacca tatctggaca gccaacgagc cgcatgcagg   540
tgtcattatg aagaaaaaac tgatctttaa                                   570
```

<210> SEQ ID NO 27
<211> LENGTH: 167
<212> TYPE: PRT
<213> ORGANISM: Homo sapiens

<400> SEQUENCE: 27

```
Gln Glu Gln Ala Gln Thr Thr Asp Trp Arg Ala Thr Leu Lys Thr Ile
```

```
1               5                   10                  15
Arg Asn Gly Val His Lys Ile Asp Thr Tyr Leu Asn Ala Ala Leu Asp
                20                  25                  30

Leu Leu Gly Gly Glu Asp Gly Leu Cys Gln Tyr Lys Cys Ser Asp Gly
            35                  40                  45

Ser Lys Pro Phe Pro Arg Tyr Gly Tyr Lys Pro Ser Pro Pro Asn Gly
        50                  55                  60

Cys Gly Ser Pro Leu Phe Gly Val His Leu Asn Ile Gly Ile Pro Ser
65                      70                  75                  80

Leu Thr Lys Cys Cys Asn Gln Ile Asp Arg Cys Tyr Glu Thr Cys Gly
                85                  90                  95

Lys Ser Lys Asn Asp Cys Asp Glu Glu Phe Gln Tyr Cys Leu Ser Lys
                100                 105                 110

Ile Cys Arg Asp Val Gln Lys Thr Leu Gly Leu Thr Gln His Val Gln
            115                 120                 125

Ala Cys Glu Thr Thr Val Glu Leu Leu Phe Asp Ser Val Ile His Leu
        130                 135                 140

Gly Cys Lys Pro Tyr Leu Asp Ser Gln Arg Ala Ala Cys Arg Cys His
145                 150                 155                 160

Tyr Glu Glu Lys Thr Asp Leu
                165
```

<210> SEQ ID NO 28
<211> LENGTH: 504
<212> TYPE: DNA
<213> ORGANISM: Homo sapiens

<400> SEQUENCE: 28

```
caggagcagg cccagaccac cgactggaga gccaccctga agaccatccg gaacggcgtt    60
cataagatag acacgtacct gaacgccgcc ttggacctcc tgggaggcga ggacggtctc   120
tgccagtata aatgcagtga cggatctaag cctttcccac gttatggtta taaaccctcc   180
ccaccgaatg gatgtggctc tccactgttt ggtgttcatc ttaacattgg tatcccttcc   240
ctgacaaagt gttgcaacca aatcgacagg tgctatgaga cctgtggcaa aagcaagaat   300
gactgtgatg aagaattcca gtattgcctc tccaagatct gccgagatgt acagaaaaca   360
ctaggactaa ctcagcatgt tcaggcatgt gaaacaacag tggagctctt gtttgacagt   420
gttatacatt taggttgtaa accatatctg gacagccaac gagccgcatg caggtgtcat   480
tatgaagaaa aaactgatct ttaa                                          504
```